(12) United States Patent
van Putten et al.

(10) Patent No.: US 11,578,046 B2
(45) Date of Patent: Feb. 14, 2023

(54) PROCESS FOR THE CONVERSION OF A SOLID LIGNOCELLULOSIC MATERIAL

(71) Applicant: Furanix Technologies B.V., Amsterdam (NL)

(72) Inventors: Robert-Jan van Putten, Amsterdam (NL); Benjamin McKay, Amsterdam (NL); Gerardus Johannes Maria Gruter, Amsterdam (NL); Jan Cornelis van der Waal, Amsterdam (NL)

(73) Assignee: Furanix Technologies B.V., Amsterdam (NL)

( * ) Notice: Subject to any disclaimer, the term of this patent is extended or adjusted under 35 U.S.C. 154(b) by 174 days.

(21) Appl. No.: 16/965,756

(22) PCT Filed: Jan. 31, 2019

(86) PCT No.: PCT/EP2019/052425
§ 371 (c)(1),
(2) Date: Jul. 29, 2020

(87) PCT Pub. No.: WO2019/149843
PCT Pub. Date: Aug. 8, 2019

(65) Prior Publication Data
US 2021/0032217 A1  Feb. 4, 2021

(30) Foreign Application Priority Data
Jan. 31, 2018  (NL) ........................ 2020354

(51) Int. Cl.
*C07D 307/50* (2006.01)
*C07B 63/00* (2006.01)

(52) U.S. Cl.
CPC ........... *C07D 307/50* (2013.01); *C07B 63/00* (2013.01)

(58) Field of Classification Search
CPC .................................................. C07D 307/50
See application file for complete search history.

(56) References Cited

U.S. PATENT DOCUMENTS

| | | | |
|---|---|---|---|
| 2,778,751 A | 1/1957 | Riehm | |
| 2,945,777 A | 7/1960 | Riehm | |
| 11,332,454 B2 * | 5/2022 | van Putten | ........... C07D 307/50 |
| 2015/0275320 A1 | 10/2015 | Schmidt et al. | |

FOREIGN PATENT DOCUMENTS

| | | | |
|---|---|---|---|
| EE | 20130003 A | 10/2014 | |
| EP | 1878480 A1 | 1/2008 | |
| FR | 3008409 A1 | 1/2015 | |
| WO | 2012/061085 A2 | 5/2012 | |
| WO | 2012/170520 A1 | 12/2012 | |
| WO | 2014/062303 A2 | 4/2014 | |
| WO | 2014/066746 A1 | 5/2014 | |
| WO | WO-2014066746 A1 * | 5/2014 | ........... C07D 307/50 |
| WO | 2015/136044 A1 | 9/2015 | |
| WO | 2018/041975 A1 | 3/2018 | |

OTHER PUBLICATIONS

Gao, et al., "Efficient One-Pot Synthesis of 5-Chloromethylfurfural (CMF) from Carbohydrates in Mild Biphasic Systems", Molecules 2013, 18, 7675-7685.
Gao, et al., "Correction: Gao, W., et al. Efficient One-Pot Synthesis of 5-Chloromethyl-furfural (CMF) from Carbohydrates in Mild Biphasic Systems. Molecules 2013, 18, 7675-7685", Molecules 2014, 19, 1370-1374.
Mascal, Mark, "Comment on Gao, W., et al. 'Efficient One-Pot Synthesis of 5-Chloromethylfurfural (CMF) from Carbohydrates in Mild Biphasic Systems'", Molecules 2013, 18, 7675-7685", Molecules 2014, 19, 1367-1369.
Vicente et al., "Oxidation of 5-chloromethylfurfural (CMF) to 2,5-diformylfuran (DFF)", Molecules (2017) vol. 22, pp. 1-14.
Mascal et al., "Dramatic Advancements in the Saccharide to 5-(Chloromethyl)furfural Conversion Reaction", published in ChemSusChem (2009), vol. 2, pp. 859-861.

* cited by examiner

*Primary Examiner* — John S Kenyon
(74) *Attorney, Agent, or Firm* — Hoffmann & Baron, LLP

(57) ABSTRACT

A process includes the following steps: a) converting a solid material containing hemicellulose, cellulose and lignin, by: (i) hydrolyzing at least part of the hemicellulose of the solid material with a first aqueous hydrochloric acid solution, yielding a remaining solid material and a hydrochloric acid-containing, aqueous, first hydrolysate product solution; (ii) hydrolyzing at least part of the cellulose of the remaining solid material with a second aqueous hydrochloric acid solution, yielding a residue and a hydrochloric acid-containing, aqueous, second hydrolysate product solution; (b) forwarding to step (c) a, hydrochloric acid-containing, aqueous intermediate product solution comprising: a part of or the whole of the hydrochloric acid-containing, aqueous first and/or second hydrolysate product solution of step (a); and (c) heating at least part of the hydrochloric acid-containing, aqueous intermediate product solution to yield a product solution containing 5-(chloromethyl)furfural, and extracting the 5-(chloromethyl)furfural from the product solution into an extraction solvent.

26 Claims, 2 Drawing Sheets

PROCESS FOR THE CONVERSION OF A SOLID LIGNOCELLULOSIC MATERIAL

CROSS-REFERENCE TO RELATED APPLICATIONS

This application is the National Stage of International Application No. PCT/EP2019/052425, filed Jan. 31, 2019, which claims the benefit of Netherlands Application No. 2020354, filed Jan. 31, 2018, the contents of which is incorporated by reference herein.

FIELD OF THE INVENTION

The present invention relates to a process, more specifically the invention relates to a process for the conversion of a solid lignocellulosic material.

BACKGROUND TO THE INVENTION

In recent times use of sustainable resources, such as biomass, is becoming increasingly important for the production of compounds for fuel and chemical applications. Such bio-derived fuels and chemicals are also sometimes referred to as "biofuels" and "biochemicals". One of the advantages of using sustainable biomass resources is that the $CO_2$ balance is more favorable as compared with a conventional feedstock of a mineral source. The production of biofuels and biochemicals from a non-edible sustainable resource, such as solid lignocellulosic material, is preferred, as such non-edible solid lignocellulosic material does not compete with food production.

5-(Chloromethyl)furfural (CMF) is a valuable intermediate in the production of biofuels and biochemicals. It can be used as an intermediate in the production of, for example, 5-(hydroxymethyl)furfural (HMF), 5-(alkoxymethyl)furfural and/or 2,5 di-formylfuran (DFF), also referred to as 2,5-furandicarbaldehyde.

2,5-Di-formylfuran may serve as a monomer or cross-linking agent in the preparation of polymers, but can also be used as a binding agent, as a corrosion-inhibiting agent or as a surface treatment agent for certain metals. It can also be used as a precursor for 2,5-furan-dicarboxylic acid (FDCA), a monomer building block for the production of bio-based polyethylenefuranoate (PEF). 2,5-Di-formylfuran can be produced from 5-(chloromethyl)furfural as described, for example, in French patent application no. FR3008409. The oxidation of 5-chloromethylfurfural to 2,5-diformylfuran is described in the article of Vicente et al., titled "Oxidation of 5-chloromethylfurfural to 2,5-diformylfuran", published in Molecules (2017) vol. 22, page 329 and following.

5-(Alkoxymethyl)furfural compounds are interesting both for fuel (additives) and chemical applications. For example, 5-(ethoxymethyl) furfural (EMF) is an interesting diesel fuel additive. Further, for example 5-(methoxymethyl)furfural (MMF) is an important intermediate in the production of 2,5-furan-dicarboxylic acid (FDCA). Estonian patent application EE2013/0003A describes a method for the preparation of 5-(alkoxymethyl)furfurals from 5-(chloromethyl)furfural or 5-(bromomethyl)furfural.

It is therefore desirable to have a process that would allow one to produce 5-(chloromethyl)furfural from a solid lignocellulosic material.

The article by Mascal et al. titled "Dramatic Advancements in the Saccharide to 5-(Chloromethyl)furfural Conversion Reaction", published in ChemSusChem (2009), vol 2, pages 859-861, describes a process for the conversion of corn stover into 5-(chloromethyl)furfural in a biphasic reactor, for example by heating powdered corn stover, concentrated hydrochloric acid (HCl) and 1,2-dichloroethane with vigorous stirring at 80° C.

The process as described by Mascal has as disadvantage that, when a solid lignocellulosic material is used as a feedstock, not only the cellulose fraction, which is the main CMF precursor, is heated in concentrated HCl, but also fractions that may not yield CMF.

Solid lignocellulosic materials contain not only cellulose, but also contain hemicellulose and lignin. Under the conditions of the above Mascal process the hemicellulose is converted into various pentoses (C5-saccharides) and hexoses (C6 saccharides). Such pentoses and hexoses can react further with various reactivities to a variety of side-products, such as furfural, 5-(hydroxymethyl)furfural, levulinic acid, formic acid and humins. In addition, such pentoses and hexoses and/or these side-products can in turn react with lignin in various types of reactions resulting in further, non-profitable, side-products and/or contaminants. Depending on market demand, the production of some side-products such as furfural, can be economically interesting. The production of non-profitable side-products and/or contaminants is, however, not desired.

Different types of solid lignocellulosic materials can vary greatly in their composition and structure. For example, paper waste will have a different composition than agricultural waste, which in its turn will have a different composition than forestry products and/or forestry residues such as wood and wood-related materials. Hardwoods may for example have greater amounts of cellulose whereas a solid lignocellulosic material such as wheat straw has more hemicellulose. Softwoods tend to contain more lignin (usually about 27-29 wt %, based on the total weight of the softwood) than hardwoods (usually about 22 wt %, based on the total weight of the hardwood). Lignocellulosic materials may further vary in particle size and brittleness. In addition the structure and/or composition of a lignocellulosic material may vary with part of the plant (e.g. bark, root or branches), age, stage of growth or other conditions in the plant's life.

For a hydrolysis process, the differences in the hemicellulose composition are most important. Hardwood hemicellulose may contain mainly xylose (a furfural precursor) while softwood hemicellulose hardly contains any xylose. A complete hydrolysis of these wood types may therefore yield large amounts of furfural in case of a hardwood feedstock and hardly any furfural in case of a softwood feedstock.

Further, different types of wood may contain different amounts of cellulose and hemicellulose. In addition, as illustrated in Table 5-1 of Fengel & Wegener in their handbook titled "Wood: Chemistry, ultrastructure, reactions," (1984) published by Walter De Gruyter, Berlin-New York, different types of wood may contain different types and amounts of non-glucosic units in the hemicellulose fraction. Non-glucosic units are monomer units other than glucose-based monomer units.

On the one hand, some non-glucosic units that can be present in a hemicellulose fraction of a solid lignocellulosic material, such as mannose, fructose and sorbose, can be reacted to produce 5-(chloromethyl)furfural. (see for example the article of Gao et al., titled "Efficient One-Pot Synthesis of 5-Chloromethylfurfural (CMF) from Carbohydrates in Mild Biphasic Systems" published in Molecules (2013), vol. 18(7), pages 7675-7685.). On the other hand, other non-glucosic units that can be present in a hemicellulose fraction of a solid lignocellulosic material can react with various reactivities to a variety of side-products.

Depending on the market demand for such side-products, such as furfural, such side-production may or may not be desirable.

The availability of different types of lignocellulosic materials may vary from country to country and even between regions within the same country. In addition the availability of the types of lignocellulosic materials may vary during the year from season to season. The process as described by Mascal lacks flexibility in respect of the type of solid lignocellulosic material used as a feedstock. No matter which solid lignocellulosic material is used as a feedstock, all fractions of the lignocellulosic material are heated at a high temperature in the presence of the concentrated hydrochloric acid as described above. Even if such solid lignocellulosic material contains a large hemicellulosic fraction and/or a large lignin fraction that may lead to substantial production of non-profitable side products.

When converting a whole solid lignocellulosic material in a process as described by Mascal, valuable energy, reactants and reactor volume is spent on producing non-profitable side-products. In a commercial-scale process such non-profitable side-products would further have to be repeatedly removed, making the overall process complex, expensive and economically unattractive. In addition, some of these side products can have a similar solubility as 5-(chloromethyl)furfural in the solvent such as 1,2-dichloroethane as used in the Mascal process, further complicating the isolation and purification of the 5-(chloromethyl)furfural and further decreasing the economical attractiveness of the process.

The residual lignin produced in a Mascal process is also disadvantageous. Residual lignin from a biomass-degradation process is normally incinerated. However, any residual lignin obtained after treatment with concentrated hydrochloric acid at high temperatures in a process as described by Mascal can contain high concentrations of covalently bound chlorine. This makes such residual lignin produced in a Mascal process less interesting for incineration.

Further the Mascal process requires powdering of the solid lignocellulosic feedstock and very vigorous stirring of the reaction mixture. The reduction of the particle size of a solid lignocellulosic feedstock to a powder and vigorous stirring of a reaction mixture may be handled relatively easy at laboratory scale but can be very cumbersome and energy-consuming when handling large amounts of feedstock at a commercial scale, especially when stirring under the highly corrosive conditions of concentrated hydrochloric acid at elevated temperature.

WO2014/066746 describes methods to produce 5-(halomethyl)furfural, including 5- (chloromethyl)furfural, by acid-catalyzed conversion of biomass. It is described that the biomass may be pretreated to help make the sugars in the biomass more accessible, by disrupting the crystalline structures of cellulose and hemicellulose and breaking down the lignin structure (if present). Common pretreatments mentioned include mechanical treatment (e.g., shredding, pulverizing, grinding), concentrated acid and dilute acid. In the exemplified process a biomass containing cellulose and/or hemicellulose is added to a reactor and contacted with solvent and aqueous hydrochloric acid. Reaction temperatures between 30° C. and 300° C. are mentioned. However, also in this process, all of hemicellulose, cellulose and lignin are present as part of the feedstock. Commercialization of this process thus suffers from the same disadvantages and complications as the Mascal process.

It would be an advancement in the art to provide a process suitable for the conversion of a solid lignocellulosic material to 5-(chloromethyl)furfural, that is flexible in its production of a side-products, such as furfural, for example depending on market demand. Such flexibility can also allow one to ensure that the highest efficiency can be obtained on the basis of the available amount of wood. In addition, it can be advantageous if such a process could be operated in a continuous or semi-continuous manner and/or could be operated at a commercial-scale in an economically attractive manner.

SUMMARY OF THE INVENTION

Such a process has now been obtained with the process according to the invention. Accordingly the present invention provides a process, which process includes the following steps:

a) converting a solid material containing hemicellulose, cellulose and lignin, by:

(i) hydrolyzing, at a temperature equal to or less than 40° C., preferably equal to or less than 30° C., at least part of the hemicellulose of the solid material with a first aqueous hydrochloric acid solution, which first aqueous hydrochloric acid solution has a hydrochloric acid concentration in the range from equal to or more than 15.0 wt. % to less than 40.0 wt. %, based on the weight amount of water and hydrochloric acid in such first aqueous hydrochloric acid solution, yielding a remaining solid material and a hydrochloric acid-containing, aqueous, first hydrolysate product solution;

(ii) hydrolyzing, at a temperature equal to or less than 40° C., preferably equal to or less than 30 ° C., at least part of the cellulose of the remaining solid material with a second aqueous hydrochloric acid solution, which second aqueous hydrochloric acid solution has a hydrochloric acid concentration in the range from equal to or more than 40.0 wt. % to equal to or less than 51.0 wt. %, based on the weight amount of water and hydrochloric acid in such second aqueous hydrochloric acid solution, yielding a residue and a hydrochloric acid-containing, aqueous, second hydrolysate product solution.

(b) forwarding to step (c) a, hydrochloric acid-containing, aqueous intermediate product solution comprising:

a part of or the whole of the hydrochloric acid-containing, aqueous first hydrolysate product solution of step (a); and/or a part of or the whole of the, hydrochloric acid-containing, aqueous second hydrolysate product solution of step (a); and (c) heating at least part of the hydrochloric acid-containing, aqueous intermediate product solution to a temperature equal to or more than 60° C., yielding a product solution containing 5-(chloromethyl)furfural, and extracting the 5-(chloromethyl)furfural from such product solution into an extraction solvent.

The process according to the invention is advantageously flexible in converting different types of solid lignocellulosic material to 5-(chloromethyl)furfural and can be easily scaled up to an economically attractive commercial-scale process. The process can further be suitably operated in a continuous or semi-continuous manner as described in more detail below.

The process according to the invention advantageously allows one to select a part or the whole of the hydrochloric acid-containing, aqueous first hydrolysate product solution and/or the, hydrochloric acid-containing, aqueous second hydrolysate product solution of step (a) for heating in step (c), depending on the type, structure and/or composition of the lignocellulosic material used as a feedstock to the process. This allows one to regulate the amount and type of side-products made, depending on the market demand for 5-(chloromethyl)furfural and such side-products, such as for example furfural.

In addition, it conveniently allows one to make better use of the sugars contained in the wood. If so desired mainly C6 saccharides can be forwarded to step (c), enabling one to use at least part of the C5 saccharides, such as xylose, to produce other valuable products, such as xylitol.

In the process according to the invention, lignin can be elegantly removed before the production of 5-(chloromethyl)furfural. In addition, also undesired impurities entrained in the lignin can be removed in this way. Further, if so desired, also the first hydrolysate product derived from the hemicelluose can be elegantly removed before the production of 5-(chloromethyl)furfural. Thus, the disadvantages and complications of the Mascal process and the process described in WO2014/066746 can be avoided.

Further step (a) of the process according to the invention can be carried out at a lower temperature than the Mascal process or the process described in WO2014/066746. Thus, the amount of heat spent on producing non-profitable side-products can be reduced. Any residual lignin retrieved from the process according to the invention can be expected to be lower in covalently bound chlorine.

In addition, the process according to the invention allows for a very economical separation of the hydrochloric acid. Hydrochloric acid is a compound that is cumbersome and expensive to separate from saccharides, such as the saccharides in an aqueous hydrolysate solution. When forwarding the hydrochloric acid-containing aqueous hydrolysate solution directly into step (c), without separating the hydrochloric acid, expensive and cumbersome process steps for the removal of hydrochloric acid, when isolating the saccharides, are no longer needed and can be avoided. After conversion of at least part of the saccharides in the aqueous hydrolysate solution to 5-(chloromethyl)furfural, such 5-(chloromethyl)furfural can be isolated in an easy and economically attractive manner by means of the mentioned extraction in step (c). As explained in more detail below, the extraction of the 5-(chloromethyl)furfural from the product solution into an extraction solvent in step (c) advantageously further increases the economic attractiveness of the process.

The 5-(chloromethyl)furfural may or may not be separated from the extraction solvent. Subsequently the 5-(chloromethyl)furfural, whether or not in the presence of the extraction solvent, may suitably be used in a subsequent process for the production of 2,5 di-formylfuran (DFF), 5-(hydroxymethyl)furfural (HMF) and/or 5-(alkoxymethyl) furfurals, such as 5-(methoxymethyl)furfural (MMF) or 5-(ethoxymethyl)furfural (EMF).

DETAILED DESCRIPTION OF THE INVENTION

Figure 1:
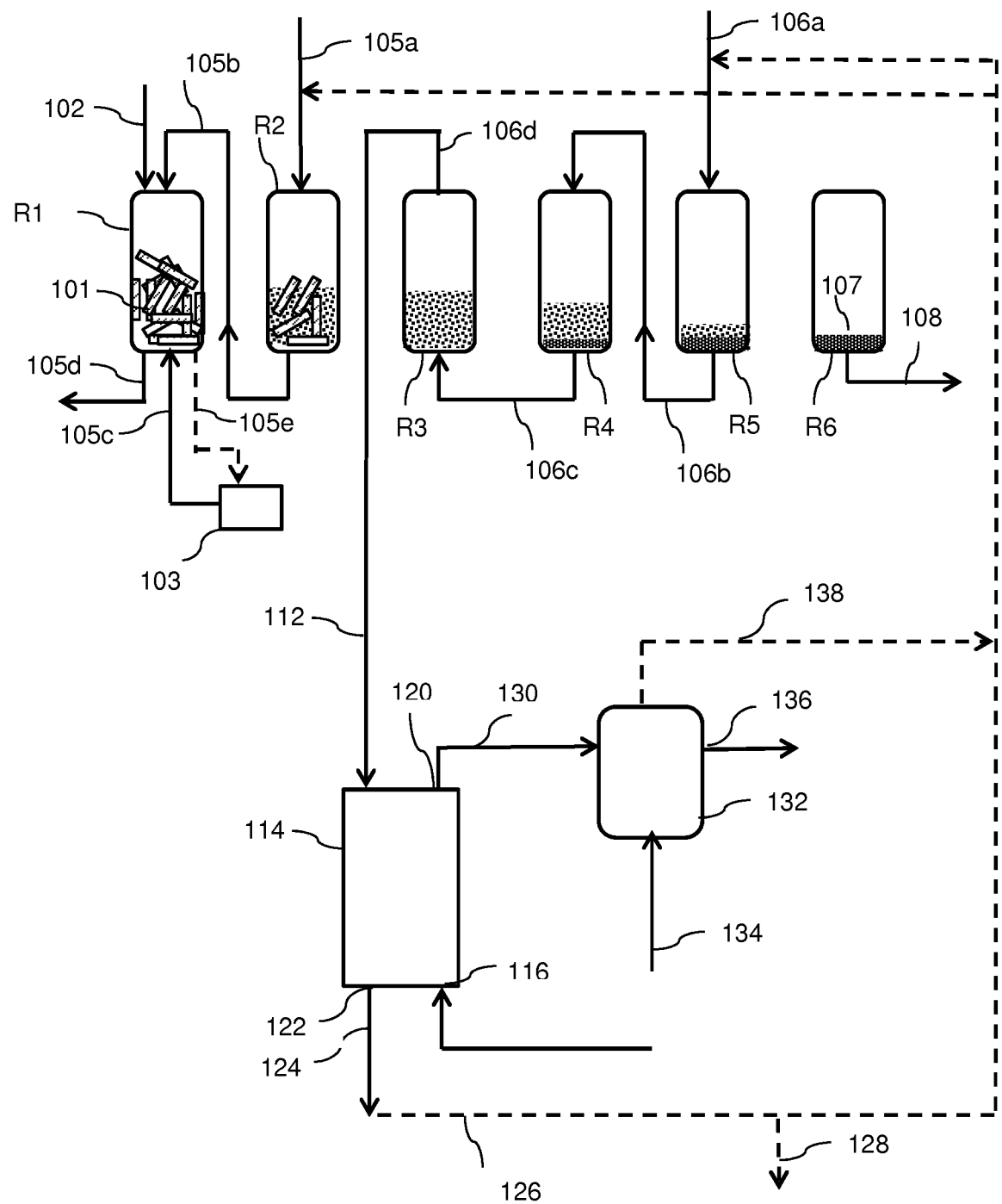
FIG. 1 illustrates a first cycle, starting at a time "t", of a process according to the invention wherein step (a) is carried out semi-continuously in a plurality of reactors and wherein step (c) of the process is carried out continuously in the presence of an extraction solvent in a counter-current biphasic continuous flow reactor.

Step (a) relates to the conversion of a solid material containing hemicellulose, cellulose and lignin. Suitably such solid material is a solid lignocellulosic material.

By cellulose (also herein referred to as cellulosic material) is herein understood a homopolysaccharide comprising glucose-based monomer units, such as cellobiose.

Hemicellulose (also herein referred to as hemicellulosic material) is also a polysaccharide, but differs from cellulose. Hemicelluloses may for example comprise pentose monomer units, such as xylose and arabinose, hexose monomer units, such as glucose and mannose, hexuronic acid and deoxy-hexose based monomer units. Whereas some hemicelluloses may essentially consist of only one single type of monomer unit (for example xylans comprising essentially only xylose), most hemicelluloses may comprise several different types of monomer units (such as for example glucomannans comprising glucose and mannose).

The process according to the invention can use a wide variety of solid lignocellulosic materials as feedstock. Examples of solid lignocellulosic materials that may suitably be used in the process of the invention include for example agricultural wastes such as stover (for example corn stover and soybean stover), corn cobs, rice straw, rice hulls, oat hulls, corn fibre, cereal straws such as wheat, barley, rye and oat straw; grasses; forestry products and/or forestry residues such as wood and wood-related materials such as sawdust and bark; waste paper; sugar processing residues such as bagasse and beet pulp; or mixtures thereof. More preferably the solid lignocellulosic material is selected from the group consisting of wood, sawdust, bark, straw, hay, grasses, bagasse, corn stover and/or mixtures thereof.

Preferably the solid lignocellulosic material is non-edible, to prevent the process from being in competition with food-production. Most preferably the solid lignocellulosic material comprises or consists of wood. The wood may include soft wood and/or hard wood and may originate from all types of trees, including spruce, pine, willow, larch, oak, birch, poplar, eucalyptus and other trees.

As explained above, different types of wood may contain different amounts of cellulose and hemicellulose. In addition, as illustrated in Table 5-1 of Fengel & Wegener in their handbook titled "Wood: Chemistry, ultrastructure, reactions," (1984) published by Walter De Gruyter, Berlin-New York, different types of wood may contain different types and amounts of non-glucosic units in the hemicellulose fraction. Depending on market demand for certain side-products some types of wood may be more preferred than others.

For example, in the process according to the invention furfural can conveniently be co-produced from xylose. If there is a substantial market demand for furfural, the solid lignocellulosic material is preferably wood or a wood-related material, having equal to or more than 10 wt. % (weight percent) xylose units, based on the total weight of its non-glucosic units in the hemicellulose fraction. Examples of suitable wood types for this purpose include Acer rubrum, Betula alleghaniensis, Betula papyrifera, Betula verrucosa, Fagus grandibtia, Fraxinus excelsior, Populus tremuloides, Robinia pseudoacacia and Ulmus Americana. The hydrochloric acid-containing, aqueous first hydrolysate product solution yielded in step (a) will then suitably contain saccharides containing xylose. When forwarding such aqueous first hydrolysate product solution to step (c), the process according to the invention conveniently allows one to co-produce furfural.

The first hydrolysate product solution is herein also sometimes referred to as simply "first hydrolysate", "first hydrolysate product" or "prehydrolysate product".

A feedstock containing epimers of glucose, such as mannose or galactose, in the hemicellulose fraction may increase the 5-(chloromethyl)furfural yield relative to the 5-(chloromethyl)furfural yield obtained on the basis of the cellulose fraction only. In such a case the lignocellulosic material is preferably wood or a wood-related material, comprising equal to or more than 10 wt. % mannose units, based on the total weight of its non-glucosic units in its hemicellulose fraction. Examples of suitable wood types for this purpose include Abies balsamea, Larix decidua, Larix laricina, Picea abies, Picea glauca, Pinus sylvestris and Tsugo Canadensis.

If it is desired to produce 5-(chloromethyl)furfural and minimize side-product make, preferably a lignocellulosic material containing a low amount of hemicellulose can be used.

Advantageously, the staged conversion in step (a) allows one to use any kind of lignocellulosic material. If in step (b) only part or whole of the hydrochloric acid-containing, aqueous second hydrolysate product solution is forwarded, whilst not forwarding the first hydrolysate product solution, advantageously the saccharides provided to step (c) will comprise predominantly glucose-based saccharides.

The solid lignocellulosic material may conveniently be washed, dried, roasted, torrefied and/or reduced in particle size before it is used as a feedstock in step (a). The solid lignocellulosic material may conveniently be supplied or be present in a variety of forms, including chips, pellets, powder, chunks, briquettes, crushed particles, milled particles, ground particles or a combination of two or more of these. When the solid lignocellulosic material is wood, it can for example be supplied or be present in the form of wood powder, wood chips, wood pellets, wood briquettes, wood chunks or a combination of two or more of these.

Preferably the solid lignocellulosic material in the present process is a solid lignocellulosic material of which the particles prior to step (a) preferably have a particle size of at least P16A and at most P100, preferably P45A or P45B, conforming European standard EN 14961-1 on solid biofuels. Alternatively, the solid lignocellulosic material in the present process is a solid lignocellulosic material of which the particles prior to step (a) preferably have a minimum size of 3 mm and maximum size of 100 mm, and more preferably have a size of between 8 mm and 45 mm, as measured following European standard EN 15149 on solid biofuels.

When the solid lignocellulosic material is wood, such wood is most preferably supplied or present in the form of wood chips. When the solid lignocellulosic material comprises grass, bagasse and/or stover, such grass, bagasse and/or stover is most preferably supplied or present in the form of pellets. Such pellets advantageously provide unstructured biomass, such as grass, bagasse and/or stover, with a desired morphology. Such morphology can advantageously limit the collapse of the material inside the reactors upon hemicellulose and cellulose hydrolysis, which otherwise could result in an undesired pressure drop.

The solid lignocellulosic material is preferably packed in a vertical tubular reactor. The reactor can suitably be provided with a discharge opening that can be opened and closed, to allow for discharge of any residue remaining of the lignocellulosic material after the process. Preferably such a discharge opening is located at the bottom of such a reactor.

The solid lignocellulosic material can be provided to a reactor in any manner known to be suitable therefore by the person skilled in the art. The lignocellulosic material can for example be provided to a reactor by means of a feed hopper, conveyer belt, screw feeder or a combination thereof. The lignocellulosic material may suitably be loaded into such a reactor in a batch-wise, semi-continuous or continuous manner. The lignocellulosic material can be loaded into a reactor via one or more inlets located at the top of such a reactor, at the bottom of such a reactor and/or via one or more lateral inlets located in the reactor wall.

Different types of reactor can be used. The process according to the invention can be carried out in any reactor known by the person skilled in the art to be suitable for a hydrolysis reaction. Such reactors are herein also referred to as "hydrolysis reactor(s)".

Preferably the process is carried out in one or more reactors as described for a Bergius-Rheinau process. Preferably such a reactor comprises a cylindrical vessel with its axis arranged in an essentially vertical or essentially horizontal manner. Preferably the reactor is an essentially vertical, tubular reactor. If so desired, the reactor may be slightly tilted such as for example described in US20150275320. Preferably the reactor is conically tapered at the top and bottom. The ratio of diameter to height may suitably range from equal to or more than 1:10 (diameter:height) to equal to or less than 1:4 (diameter:height). The reactor can suitably be provided with a discharge opening that can be opened and closed, to allow for discharge of any residual lignin after the process. Preferably such a discharge opening is located at the bottom of such a reactor. Examples of suitable reactors include the reactors as described in for example U.S. Pat. No. 2,778,751, EP1878480, WO2015/136044 and non-prepublished PCT/EP2017/071914. The aqueous hydrochloric acid solutions can advantageously flow through such hydrolysis reactors in an intermittent, continuous or semi-continuous manner.

Step (a) is preferably carried out in a plurality of reactors, more preferably in a plurality of reactors connected in series. Such plurality of reactors is herein also referred to as a reactor sequence. Preferably, step (a) is carried out in a plurality of reactors (also referred to as columns) connected in series as described for a Bergius-Rheinau process. Examples of the Bergius-Rheinau process include the Bergius-Rheinau process, preferably as amended by Riehm, as described in for example U.S. Pat. No. 2,778,751. It is also possible for step (a) to be carried out as described in WO2012/061085.

Step (i) of step (a) is preferably preceded by a loading step wherein a solid lignocellulosic material is loaded into the reactor as described in more detail above.

Step (i) suitably comprises hydrolyzing, at a temperature equal to or less than 40° C., preferably equal to or less than 30° C., at least part of the hemicellulose of the solid material with a first aqueous hydrochloric acid solution, which first aqueous hydrochloric acid solution has a hydrochloric acid concentration in the range from equal to or more than 15.0 wt. % to less than 40.0 wt. %, based on the weight amount of water and hydrochloric acid in such first aqueous hydrochloric acid solution. Such step (i) suitably yields a first hydrolysate product solution. In addition there will be remaining solid material. Such remaining solid material can suitably still comprise cellulose and lignin.

By hydrolyzing, respectively hydrolysis, is herein understood the breaking of bonds between saccharide units in a polysaccharide, such as hemicellulose or cellulose, to yield monosaccharides, disaccharides and/or oligosaccharides (by oligo-saccharides are herein understood saccharide chains comprising in the range from 3 to 10 mono-saccharide units). The product(s) of a hydrolysis are also referred to as "hydrolysate".

The hydrolysis of hemicellulose is also known as "pre-hydrolysis" and the products of the hydrolysis of hemicellulose are also known as "pre-hydrolysate". Step (i) can therefore herein also referred to as "pre-hydrolysis" or "pre-hydrolyzing". The first hydrolysate product solution obtained by hydrolysis of the hemicellulose in step (i) can herein also referred to as "pre-hydrolysate product", "pre-hydrolysate product solution" or "hemicellulose hydrolysate product solution". The remaining solid material after the hydrolysis of the hemicellulose in step (i) can herein also be referred to as "pre-hydrolyzed solid material".

As illustrated by the hydrochloric acid concentration, the conditions for the pre-hydrolysis of step (i) are less severe than the conditions for the main hydrolysis of step (ii) described below. Under the conditions of step (i), hemicellulose can be selectively hydrolyzed. The hydrolyzing of the hemicellulose can already be effected by the mere contacting of the solid lignocellulosic material with the first aqueous hydrochloric acid solution. To obtain the best results, the solid material is preferably soaked in first aqueous hydrochloric acid solution. Such first aqueous hydrochloric acid solution may or may not contain saccharides.

Step (i) can be carried out over a wide range of pressures. Conveniently a pressure of about 0.1 MegaPascal (corresponding to about 1 bar) can be applied. All pressures herein are absolute pressures.

An elevated temperature is not required. Step (i) can therefore conveniently be carried out at about ambient temperature (20° C.). For practical purposes step (i) is preferably carried out at a temperature equal to or more than 0° C. and preferably equal to or less than 30° C. It is believed that at temperatures higher than 40° C., cellulose may start to become hydrolyzed and hence selectivity towards hemicellulose hydrolysis may decrease. In addition, such hydrolysis of cellulose may lead to lower yields in step (ii).

The hydrochloric acid concentration for the first aqueous hydrochloric acid solution as indicated above is based on the weight amount of water and hydrochloric acid contained in the first aqueous hydrochloric acid solution. Preferably the first aqueous hydrochloric acid solution has a hydrochloric acid concentration in the range from equal to or more than 34.0 wt. % to equal to or less than 39.9 wt. %, more preferably in the range from in the range from equal to or more than 36.0 wt. % to equal to or less than 39.0 wt. %, based on the weight amount of water and hydrochloric acid contained in the first aqueous hydrochloric acid solution.

The combination of pressure, temperature and hydrochloric acid concentration can be optimized to achieve optimal selectivity in the hydrolysis of hemicellulose. Preferably a combination of pressure, temperature and hydrochloric acid concentration is applied such that the hydrochloric acid remains completely dissolved in the solution as hydrogen ions and chloride ions. More preferably the combination of pressure, temperature and hydrochloric acid concentration is such that no molecular hydrochloric acid remains in solution. Further guidance on this aspect can for example be found by plotting the boiling point of an aqueous hydrochloric acid solution as a function of the hydrochloric acid concentration at the applied pressure. Such a plot has for example been provided on the website of "The Dietrich Process Systems", on "Isothermal Absorption of Hydrogen Chloride", pages 1-2, found on the internet under URL: https://www.dedietrich.com/en/solutions-and-products/halide-treatment/hcl-treament/absorption-hydrogen-chloride/isothermal, on 30 January 2018. The combination of pressure, temperature and hydrochloric acid concentration applied during step (i) is most preferably such that the boiling point is not exceeded.

For practical purposes it is preferred that, suitably at a pressure of about 0.1 MegaPascal, the result of multiplying the temperature (in ° C.) with the weight percentage (wt. %) hydrochloric acid concentration, based on the weight amount of water and hydrochloric acid contained in the first aqueous hydrochloric acid solution, is equal to or less than 1000. This is illustrated by formula (I) below $$\text{Temperature (° C.)} \times \text{concentration (wt. \%)} \leq 1000 \quad \text{(I)}$$

Without wishing to be bound by any kind of theory it is believed that during the pre-hydrolysis in step (i), predominantly any hemicellulose present in solid material can be hydrolyzed. This may suitably result in a first hydrolysate product solution that may comprise or consist of an aqueous solution containing hydrochloric acid and a mixture of mono- di- and oligo-saccharides of pentoses (i.e. $C_5$-saccharides, that is, sugars whose molecules contain five carbon atoms) and hexoses (i.e. $C_6$-saccharides, that is, sugars whose molecules contain six carbon atoms).

The first hydrolysate product solution may include for example pentose monosaccharides, hexose monosaccharides, pento se disaccharides, hexose disaccharides, and pentose-hexose disaccharides, pentose oligosaccharides, hexose oligosaccharides and/or oligosaccharides of mixtures of pentoses and hexoses. Suitably the first hydrolysate product solution can comprise one or more compounds selected from the group consisting of glucose, fructose, mannose, galactose, arabinose, xylose, sucrose, cellobiose, ribulose, ribose, lyxose, allose, altrose, glucose dimers (such as maltose), glucose trimers, cellotriose, maltotriose, cellodextrins, dextrins, xylan-oligosaccharides, mannan-oligosaccharides, arabinan-oligosaccharides and oligofructans. More suitably the first hydrolysate product solution can comprise at least one compound selected from the group consisting of mannose, glucose, galactose, arabinose and xylose or their dimers or oligomers.

Preferably the first hydrolysate product solution contains a total amount of saccharides (including mono-, di- and/or oligosaccharides) of equal to or more than 2 wt. % saccharides, more preferably of equal to or more than 5 wt. % saccharides, still more preferably of equal to or more than 10 wt. % saccharides, and most preferably of equal to or more than 20 wt. % saccharides, based on the total weight of the pre-hydrolysate product solution. The upper limit for the saccharide content in the first hydrolysate product solution is formed by the solubility of the saccharides in the solution. For practical purposes the first hydrolysate product solution may suitably contain a total amount of saccharides (including mono-, di- and/or oligosaccharides) of equal to or less than 45 wt. %, more preferably of equal to or less than 40 wt. % saccharides, based on the total weight of the pre-hydrolysate product solution.

In addition to the saccharides, the first hydrolysate product solution can suitably contain hydrochloric acid. Preferably, the first hydrolysate product solution can have a hydrochloric acid concentration in the range from equal to or more than 1.0 wt. % to equal to or less than 40.0 wt. %, more preferably in the range from equal to or more than 10.0 wt.

% to equal to or less than 39.0 wt. %, based on the weight of the combination of hydrochloric acid and water in the first hydrolysate product solution.

The remaining solid material, also referred to as prehydrolyzed solid material, may suitably comprise predominantly lignin and cellulose. Preferably the remaining solid material contains mere minor amounts or essentially no hemicellulose. Preferably, the hemicellulose content of solid material used as a feedstock to the process has been reduced by at least at least 85 wt. %, more preferably at least 95 wt. %, and preferably essentially 100 wt.%. That is, preferably at least 85 wt. %, more preferably at least 95 wt. %, and most preferably essentially 100 wt.% of the hemicellulose in the solid material used as a feedstock is hydrolyzed in step (i). The remaining solid material may thus comprise equal to or less than 10 wt. %, more preferably equal to or less than 5 wt. %, most preferably equal to or less than 1 wt. % of the hemicellulose that was present in the solid material used as a feedstock. Most preferably the remaining solid material comprises essentially no hemicellulose.

Step (ii) suitably comprises hydrolyzing, at a temperature equal to or less than 40° C., preferably equal to or less than 30° C., at least part of the cellulose of the pre-hydrolyzed solid material with a second aqueous hydrochloric acid solution, which second aqueous hydrochloric acid solution has a hydrochloric acid concentration in the range from equal to or more than 40.0 wt. % to equal to or less than 51.0 wt. %, based on the weight amount of water and hydrochloric acid in such second aqueous hydrochloric acid solution. Step (ii) suitably yields a second hydrolysate product solution and a residue.

The second hydrolysate product solution is herein sometimes also referred to as simply "second hydrolysate", "second hydrolysate product" or "main hydrolysate product".

The hydrolysis of cellulose is also known as "main hydrolysis" and the products of the hydrolysis of cellulose are also known as "main hydrolysate". Step (ii) can therefore herein also referred to as "main hydrolysis", "further hydrolysis" or "further hydrolyzing". The second hydrolysate product solution obtained by hydrolysis of the cellulose in step (ii) can herein also referred to as "main hydrolysate product", "main hydrolysate product solution", "final hydrolysate product solution" or "cellulose hydrolysate product solution".

During such main hydrolysis, a substantial part of the remaining bonds between the saccharide units in the remaining polysaccharides in the remaining solid material, are hydrolyzed. Although most preferably essentially all remaining bonds between the saccharide units in the remaining polysaccharides are broken, the advantages of the invention can also be obtained when a part of the bonds between such saccharide units remains intact.

The hydrolyzing of the cellulose in the remaining solid material in step (ii) can already be effected by the mere contacting of the remaining solid material with the second aqueous hydrochloric acid solution. To obtain the best results, the remaining solid material is preferably soaked in second aqueous hydrochloric acid solution. Such second aqueous hydrochloric acid solution may or may not contain saccharides as explained below.

Step (ii) can be carried out over a wide range of pressures. Conveniently a pressure of about 0.1 MegaPascal (corresponding to about 1 bar) can be applied.

Step (ii) can conveniently be carried out at about ambient temperature (20° C.). For practical purposes step (ii) is preferably carried out at a temperature in the range from equal to or more than 0° C. to equal to or less than 30° C.

Preferably the second aqueous hydrochloric acid solution has a hydrochloric acid concentration in the range from equal to or more than 41.0 wt. % to equal to or less than 45.0 wt. %, based on the combined weight amount of water and hydrochloric acid in the second aqueous hydrochloric acid solution.

The residue may suitably comprise predominantly lignin. Preferably the residue contains mere minor amounts or essentially no hemicellulose and mere minor amounts or essentially no cellulose. Preferably, the cellulose content of the remaining solid material (which was used at the start of step (iii) has been reduced by at least at least 85 wt. %, more preferably at least 95 wt. %, and preferably essentially 100 wt.%. That is, preferably at least 85 wt. %, more preferably at least 95 wt. %, and most preferably essentially 100 wt.% of the cellulose in the remaining solid material is hydrolyzed in step (iii). The residue may thus comprise equal to or less than 10 wt. %, more preferably equal to or less than 5 wt. %, most preferably equal to or less than 1 wt. % of the cellulose that was present in the remaining solid material. Most preferably the residue comprises essentially no cellulose and essentially no hemicellulose. The residue may in addition comprise hydrochloric acid.

The second hydrolysate product solution may suitably comprise or consist of an aqueous solution containing hydrochloric acid and predominantly glucose saccharides.

The second hydrolysate product solution can contain a total amount of saccharides (including mono-, di- and/or oligosaccharides) of equal to or more than 2 wt. % saccharides, more preferably of equal to or more than 5 wt. % saccharides, still more preferably of equal to or more than 10 wt. % saccharides, and possibly even equal to or more than 20wt. % saccharides, based on the total weight of the second hydrolysate solution. The upper limit for the saccharide content in the second hydrolysate product solution is formed by the solubility of the saccharides in the solution. For glucose, a solubility at 25° C. of 909 grams glucose per kilogram water has been reported. For practical purposes the second hydrolysate product solution may suitably contain a total amount of saccharides (including mono-, di- and/or oligosaccharides) of equal to or less than 45 wt. %, more preferably of equal to or less than 40 wt. % saccharides, based on the total weight of the second hydrolysate solution.

Most preferably the second hydrolysate product solution contains a total amount of saccharides in the range from equal to or more than 5 wt. % to equal to or less than 10 wt.%, based on the total weight of the second hydrolysate solution.

The second hydrolysate product solution may include for example glucose monosaccharides, glucose disaccharides, and glucose oligosaccharides. Suitably the second hydrolysate product solution can comprise one or more compounds selected from the group consisting of glucose and cellobiose.

The second hydrolysate product solution may comprise some, but preferably comprises little or no pentoses (C5-saccharides). Preferably, the second hydrolysate product solution contains a total amount of C5-saccharides, that is equal to or less than 20.0 wt. %, more preferably equal to or less than 10.0 wt. %, still more preferably equal to or less than 5.0 wt. %, even more preferably equal to or less than 1.0 wt. % and most preferably equal to or less than 0.1 wt. %, based on the total weight of saccharides in the second hydrolysate solution.

In addition to the saccharides, the second hydrolysate product solution will suitably contain hydrochloric acid. Preferably the second hydrolysate product solution will have a hydrochloric acid concentration in the range from equal to or more than 20.0 wt. %, more suitably equal to or more than 30.0 wt. % to equal to or less than 50.0 wt. %, more suitably equal to or less than 45.0 wt. %, more preferably in the range from equal to or more than 38.0 wt. % to equal to or less than 43.0 wt. %, based on the weight of the combination of hydrochloric acid and water.

Preferably step (a) includes:

a step (i), wherein the solid material is residing in a stationary phase within a reactor and wherein the solid material is contacted with a mobile phase that moves through such reactor, which mobile phase includes at least a zone comprising one or more portions of first aqueous hydrochloric acid solution; and/or a step (ii) wherein remaining solid material is residing in a stationary phase within a reactor and wherein the remaining solid material is contacted with a mobile phase that moves through such reactor, which mobile phase includes at least a zone comprising one or more portions of second aqueous hydrochloric acid solution Preferably such mobile phase is an intermittent, semi-continuous or continuous mobile phase.

More preferably step (a) is carried out in a plurality of reactors:

wherein in step (i) one or more portions of first aqueous hydrochloric acid solution are moving from one reactor to another and are contacted with stationary, optionally already partly pre-hydrolyzed, solid material residing in two or more reactors; and/or wherein in step (2) one or more portions of second aqueous hydrochloric acid solution are moving from one reactor to another and are contacted with stationary, optionally already partly further hydrolyzed, remaining solid material residing in two or more reactors.

More preferably the first aqueous hydrochloric acid solution is contacted counter-currently with the, optionally partly pre-hydrolyzed, solid material and/or the second aqueous hydrochloric acid solution is contacted counter-currently with the, optionally partly further hydrolyzed, remaining solid material.

In step (i) of step (a) one or more portions of first aqueous hydrochloric acid solution can conveniently form a plug or liquid column, optionally in combination with other fluids, which plug or liquid column is moving, preferably continuously or semi-continuously, through a plurality of reactors, each reactor containing an amount of, optionally already partly pre-hydrolyzed, stationary solid material. Such solid material is suitably a solid lignocellulosic material as described above. When step (i) is carried out counter-currently, one or more portions of fresh first aqueous hydrochloric acid solution may conveniently be supplied to a reactor holding solid material which has already been partly pre-hydrolyzed to the highest degree. Saccharides can be absorbed from such, already partly, pre-hydrolyzed solid material and the one or more portions of first aqueous hydrochloric acid solution (suitably now containing some saccharides) may subsequently move from the outlet of such reactor to the inlet of a preceding reactor, which preceding reactor holds solid material which has undergone less or no pre-hydrolysis.

During (i) hemicellulose is being hydrolyzed and the resulting saccharides become dissolved in the first aqueous hydrochloric acid solution. Therefore, in addition to the water and the hydrochloric acid, the first aqueous hydrochloric acid solution may or may not contain other compounds such as for example dissolved saccharides.

When freshly added to the process, the first aqueous hydrochloric acid solution (also referred to as fresh first aqueous hydrochloric acid solution) preferably comprises only minor amounts or even essentially no dissolved saccharides. After absorbing saccharides, the first aqueous hydrochloric acid solution is no longer fresh. Such a first aqueous hydrochloric acid solution that further contains dissolved saccharides is herein also referred to as "intermediate pre-hydrolysate solution" or as "intermediate pre-hydrolysate". The intermediate pre-hydrolysate solution can suitably contain saccharides (such as a mixture of $C_5$-saccharides and $C_6$-saccharides) dissolved in an aqueous hydrochloric acid solution. Such intermediate pre-hydrolysate solution may therefore suitably be an, hydrochloric acid-containing, aqueous intermediate pre-hydrolysate solution. The intermediate pre-hydrolysate solution may suitably still be used for contacting further, optionally partly pre-hydrolyzed, solid material to suitably absorb further saccharides therefrom.

Whilst moving, preferably counter-currently, from each one reactor to another reactor the first aqueous hydrochloric acid solution may suitably absorb more and more saccharides. Thus, the saccharide concentration of the first aqueous hydrochloric acid solution may suitably gradually increase until a hydrochloric acid-containing, aqueous first hydrolysate product solution is obtained.

When carried out counter-currently, step (i) is preferably carried out in a plurality of "x" reactors $FR_1$ to $FR_x$, wherein fresh lignocellulosic material can be introduced and/or residing in reactor $FR_1$ and each subsequent reactor $FR_2$ to $FR_x$ can contain partly pre-hydrolyzed lignocellulosic material, where the degree of pre-hydrolysis of the lignocellulosic material may increase in the direction of reactor $FR_2$ to $FR_x$; and wherein one or more portions of fresh first aqueous hydrochloric acid solution can be introduced in the last reactor $FR_x$ and can move from reactor $FR_x$ to reactor $FR_1$. Suitably such portions of first aqueous hydrochloric acid solution can gradually absorb saccharides from the, optionally already partly pre-hydrolyzed lignocellulosic material, to thereby produce a hydrochloric acid-containing, aqueous pre-hydrolysate solution that can be withdrawn from reactor $FR_1$. Such hydrochloric acid-containing, aqueous pre-hydrolysate solution will advantageously be more rich in saccharides than if step (i) would have been carried out in a single reactor. In reactor $FR_x$ a prehydrolyzed solid material can be obtained, that can suitably be used in step (ii).

In step (ii) of step (a) one or more portions of second aqueous hydrochloric acid solution can conveniently form a plug or liquid column, optionally in combination with other fluids, which plug or liquid column is moving, preferably continuously or semi-continuously, through a plurality of reactors, each reactor containing an amount of, optionally already partly further hydrolyzed, stationary remaining solid material.

When step (ii) is carried out counter-currently, the one or more portions of fresh second aqueous hydrochloric acid solution may conveniently be supplied to a reactor holding remaining solid material which has already been partly hydrolyzed to the highest degree. Saccharides can be absorbed from such, already partly hydrolyzed, remaining solid material and the one or more portions of second aqueous hydrochloric acid solution (suitably now containing some saccharides) may subsequently move from the outlet of such reactor to the inlet of a preceding reactor, which preceding reactor holds remaining material which has undergone less or no further hydrolysis.

During step (ii) cellulose is being hydrolyzed and the resulting saccharides become dissolved in the second aqueous hydrochloric acid solution. Therefore, in addition to the water and the hydrochloric acid, the second aqueous hydrochloric acid solution may or may not contain other compounds such as for example dissolved saccharides.

When freshly added to the process, the second aqueous hydrochloric acid solution (also referred to as fresh second aqueous hydrochloric acid solution) preferably comprises only minor amounts or even essentially no dissolved saccharides.

After absorbing saccharides, the second aqueous hydrochloric acid solution is no longer fresh. Such a second aqueous hydrochloric acid solution that further contains dissolved saccharides is herein also referred to as "intermediate hydrolysate solution" or "intermediate main hydrolysate solution". The intermediate hydrolysate solution can suitably contain saccharides (such as a mixture of $C_5$-saccharides and $C_6$-saccharides) dissolved in an aqueous hydrochloric acid solution. Such intermediate hydrolysate solution may therefore suitably be an, hydrochloric acid-containing, aqueous intermediate hydrolysate solution. The intermediate hydrolysate solution may suitably still be used for contacting further, optionally partly hydrolyzed, solid material to suitably absorb further saccharides therefrom.

Whilst moving, preferably counter-currently, from one reactor to another reactor the second aqueous hydrochloric acid solution may suitably absorb more and more saccharides. Thus, the saccharide concentration of the second aqueous hydrochloric acid solution may suitably gradually increase until a hydrochloric acid-containing, aqueous second hydrolysate product solution is obtained.

When carried out counter-currently, step (ii) is preferably carried out in a plurality of "y" reactors $SR_1$ to $SR_y$, wherein fresh pre-hydrolyzed solid material is residing in reactor $SR_1$ and each subsequent reactor $SR_2$ to $SR_y$ contains partly hydrolyzed, remaining solid material, where the degree of hydrolysis of the remaining solid material increases in the direction of $SR_2$ to $SR_y$; and wherein one or more portions of fresh second aqueous hydrochloric acid solution are introduced in the last reactor $SR_y$ and move from reactor $SR_y$ to reactor $SR_1$. Suitably such portions of second aqueous hydrochloric acid solution can gradually absorb saccharides from the, optionally already partly hydrolyzed, remaining solid material, to thereby produce a hydrochloric acid-containing, aqueous first hydrolysate solution, that can be withdrawn from reactor $SR_1$. Such hydrochloric acid-containing, aqueous hydrolysate solution will be advantageously more rich in saccharides, than if step (ii) would have been carried out in a single reactor. In reactor $SR_y$ a residue can be obtained, that can suitably be discarded from the reactor $SR_y$.

Hence, preferably step (a) comprises
(i) pre-hydrolyzing a solid lignocellulosic material, wherein the solid lignocellulosic material is contacted counter-currently with a first aqueous hydrochloric acid solution, which first aqueous hydrochloric acid solution has a hydrochloric acid concentration in the range from equal to or more than 34.0 wt % to equal to or less than 39.9 wt %, based on the combined weight amount of water and hydrochloric acid in such first aqueous hydrochloric acid solution, to thereby produce a pre-hydrolyzed lignocellulosic material and a, hydrochloric acid-containing, aqueous pre-hydrolysate product solution; and/or (ii) further hydrolyzing at least part of the pre-hydrolyzed lignocellulosic material, wherein the pre-hydrolyzed lignocellulosic material is contacted counter-currently with a second aqueous hydrochloric acid solution, which second aqueous hydrochloric acid solution has a hydrochloric acid concentration in the range from equal to or more than 40.0 wt % to equal to or less than 51.0 wt %, based on the combined weight amount of water and hydrochloric acid in such second aqueous hydrochloric acid solution, to thereby produce a residue and a, hydrochloric acid-containing, aqueous final hydrolysate product solution.

Preferably step (a) is carried out in a plurality of reactors, preferably connected in series, comprising 2 or more reactors, more preferably in the range from equal to or more than 2 to equal to or less than 16 reactors, still more preferably in the range from equal to or more than 4 to equal to or less than 8 reactors and most preferably in the range from equal to or more than 4 to equal to or less than 7 reactors.

It is possible for step (i) to be carried out in a first set of reactors connected in series and for step (ii) to be carried out in an, optionally separate, second set of reactors connected in series. Suitably each such a set of reactors comprises 2 or more reactors, preferably 2 to 10, more preferably 2 to 8 reactors and most preferably 2 to 4 reactors.

Preferably, however, step (i) and step (ii) are carried out within one combined set of reactors connected in series. Preferably such a combined set of reactors connected in series comprises 2 or more reactors, more preferably in the range from equal to or more than 2 to equal to or less than 16 reactors, still more preferably in the range from equal to or more than 4 to equal to or less than 8 reactors and most preferably in the range from equal to or more than 4 to equal to or less than 7 reactors.

After step (i) the first hydrolysate product solution can be separated from the remaining solid material and after step (ii) the second hydrolysate product solution can be separated from the residue. These separations can be carried out in any manner known to be suitable by the person skilled in the art, such as for example described in U.S. Pat. No. 2,778,751, EP1878480, WO2015/136044 and non-prepublished PCT/EP2017/071914. Preferably step (i) in step (a) further comprises separating the first hydrolysate product solution from the remaining solid material before further hydrolyzing at least part of such remaining solid material with a second aqueous hydrochloric acid solution in step (ii).

Step (a) may for example be carried out as described in U.S. Pat. No. 2,945,777. 2,945,777 describes a process for the saccharification of soft wood sawdust comprising a pre-hydrolysis step and a main hydrolysis step. In the first step the sawdust is subjected at a temperature of about 15 to 30° C. to a pre-hydrolysis with hydrochloric acid containing 34 to 37 percent of HCl by weight for a time sufficient to dissolve substantially the hemicelluloses in an amount corresponding to about 22 to 26 percent of the dry wood substance and the obtained solution is subsequently separated from the solid residue. In the second step the solid residue of said pre-hydrolysis is treated in a main hydrolysis with hydrochloric acid of about 40 to 42% HCl content and crystalline glucose is recovered from the sugar syrup obtained in said main hydrolysis.

The process according to the invention can advantageously be carried out in a continuous or semi-continuous manner. For example, the process can be carried out in a plurality of reactors in a sequence of cycles, wherein within each cycle:

at least part of the hemicellulose of a solid lignocellulosic material (that is, a solid material containing hemicellulose, cellulose and lignin) is hydrolyzed in a first reactor sequence of "x" reactors $FR_1$ to $FR_x$, wherein fresh solid lignocellulosic material is introduced in reactor $FR_1$ and each subsequent reactor $FR_2$ to $FR_x$ contains, partly pre-hydrolyzed, solid material; and wherein one or more portions of, preferably fresh, first aqueous hydrochloric acid solution are introduced in the last reactor $FR_x$ pushing forward a first liquid column, such first liquid column containing previous portions of first aqueous hydrochloric acid solution, in a counter-current direction from reactor $FR_x$ to reactor $FR_1$; yielding a remaining solid material residing in reactor $FR_x$ and a hydrochloric acid-containing, aqueous first hydrolysate product solution residing in reactor $FR_1$, whereafter the hydrochloric acid-containing, aqueous first hydrolysate product solution is recovered from reactor $FR_1$;

at least part of the cellulose of a prehydrolyzed solid material is hydrolyzed in a second reactor sequence of "y" reactors $SR_1$ to $SR_y$, wherein remaining solid material is residing in reactor $SR_1$ and each subsequent reactor $SR_2$ to $SR_y$ contains, partly hydrolyzed, remaining solid material; and wherein one or more portions of, preferably fresh, second aqueous hydrochloric acid solution are introduced in the last reactor $SR_y$ pushing forward a second liquid column, such second liquid column containing previous portions of second aqueous hydrochloric acid solution, in a counter-current direction from reactor $SR_y$ to reactor $SR_1$; yielding a residue residing in reactor $SR_y$ and a hydrochloric acid-containing, aqueous second hydrolysate product solution residing in reactor $SR_1$; whereafter the hydrochloric acid-containing, aqueous second hydrolysate product solution is recovered from reactor $SR_1$;

whereafter respective reactors $FR_1$ to $FR_{x-1}$ shift into the position previously occupied by respective reactors $FR_2$ to $FR_x$, respective reactor $FR_x$ shifts into the position previously occupied by respective reactor $SR_1$, respective reactors $SR_1$ to $SR_{y-1}$ shift into the position previously occupied by respective reactors $SR_2$ to $SR_y$, and respective reactor $SR_y$ shifts into the position previously occupied by respective reactor FRi By shifting of one reactor into the position of another reactor is herein preferably understood that the one reactor takes over the place, i.e. the function, of the other reactor in the mentioned first or second reactor sequence.

Each cycle is preferably performed within a time period referred to as the cycle period. The cycle period is suitably the time period wherein all the above listed activities are to be carried out, whereafter each reactor can shift one position in the reactor sequence (i.e. the period between reactor shifts).

The cycle period preferably lies in the range of equal to or more than 4 hours, more preferably equal to or more than 6 hours, to equal to or less than 24 hours, more preferably equal to or less than 12 hours. Most preferably the cycle period lies in the range from equal to or more than 7 hours to equal to or less than 9 hours. For example, the cycle period can be 8 hours.

The partly pre-hydrolyzed solid material initially residing in reactors $FR_2$ to $FR_x$ can conveniently be obtained in one or more previous cycle periods.

Similarly, the partly hydrolyzed, pre-hydrolyzed solid material initially residing in reactors $SR_2$ to $SR_y$ can be suitably obtained in one or more previous cycle periods.

Preferences for the reaction conditions, the lignocellulosic material, the first aqueous hydrochloric acid solution, the second aqueous hydrochloric acid solution, the first hydrolysate product solution, the second hydrolysate product solution, the pre-hydrolyzed solid material, any mobile phases and any other aspects are all as described herein above.

During a cycle period, the rate at which the reactants are provided to the reactors can vary widely, especially as some reactants such as wood may be provided to the reactors at an intermittent basis. When averaged over a full cycle period, the average weight ratio of amount of first aqueous hydrochloric acid solution to amount of solid (lignocellulosic) material (on dry basis) preferably lies in the range from equal to or more than 0.5:1 (wt/wt) to equal to or less than 10:1(wt/wt), more preferably equal to or less than 7:1 (wt/wt) and most preferably equal to or less than 5:1(wt/wt). Similarly, when averaged over a full cycle period, the average weight ratio of amount of second aqueous hydrochloric acid solution to amount of solid (lignocellulosic) material (on dry basis) preferably lies in the range from equal to or more than 0.5:1 (wt/wt) to equal to or less than 10:1(wt/wt), more preferably equal to or less than 7:1(wt/wt) and most preferably equal to or less than 5:1(wt/wt).

Step (b) comprises forwarding, directly or indirectly, to step (c) a hydrochloric acid-containing, aqueous intermediate product solution comprising:

a part of or the whole of the hydrochloric acid-containing, aqueous first hydrolysate product solution of step (a); and/or a part of or the whole of the, hydrochloric acid-containing, aqueous second hydrolysate product solution of step (a).

As explained above, the process advantageously allows one to select and forward to step (c) only first hydrolysate product solution, only second hydrolysate product solution or a combination of first hydrolysate product solution and second hydrolysate product solution.

The selection can for example be made on the basis of the lignocellulosic material used as a feedstock and market demand for side products.

For example, step (b) may suitably comprise forwarding, directly or indirectly, to step (c) a hydrochloric acid-containing, aqueous intermediate product solution comprising or consisting of only a part of or the whole of the, hydrochloric acid-containing, aqueous second hydrolysate product solution of step (a), whilst suitably not forwarding any part of or the whole of the hydrochloric acid-containing, aqueous first hydrolysate product solution of step (a).

By selecting and forwarding only second hydrolysate product solution to step (c) advantageously a more constant composition of the products (such as 5-(chloromethyl)furfural) and side-products made in step (c) can advantageously be obtained. Such a constant composition of the products and side-products is desirable when scaling up the purification of the products and removal of side-products to a commercial scale. By heating only the hydrochloric acid-containing, aqueous second hydrolysate product solution to a temperature equal to or more than 60° C., preferably equal to or more than 70° C., suitably in the absence of the first hydrolysate product solution and in the absence of the lignin, side-product make from hemi-cellulose-derived C5- and C6 saccharides and/or lignin can be reduced and energy and reactor volume can be saved. By removing the precursors of such side-products at an earlier, lower temperature, stage, a more energy-efficient and a more cost-efficient process is obtained.

Alternatively, a selection can be made for a hydrochloric acid-containing, aqueous intermediate product solution comprising both first hydrolysate product solution as well as second hydrolysate product solution to tweak the composition of the products (such as 5-(chloromethyl)furfural) and side-products (such as furfural) to meet market demand.

Preferably, part or whole of the aqueous intermediate product solution, suitably comprising both the hydrochloric acid and the saccharides, is forwarded and/or applied directly into step (c). If so desired, a small amount of water or hydrochloric acid may be added or removed to obtain the optimal hydrochloric acid concentration and/or the optimal sugar concentration for step (c).

By forwarding the aqueous intermediate product solution, suitably comprising both the hydrochloric acid and the saccharides directly into step (c), without separating the hydrochloric acid from the saccharides, expensive and cumbersome process steps for isolating the mono-saccharides first by removing such hydrochloric acid are no longer needed and can be avoided. The separation of hydrochloric acid from CMF and/or CMF derivatives after step (c) by extraction instead of evaporation is advantageous both from an economic as well as from a safety perspective.

Step (c) suitably comprises heating at least part of the hydrochloric acid-containing, aqueous intermediate product solution to a temperature equal to or more than 60° C., preferably equal to or more than 70° C. Such heating suitably yields a product solution containing 5-(chloromethyl)furfural. The 5-(chloromethyl)furfural is suitably extracted from such product solution into an extraction solvent. Step (c) is thus suitably yielding a 5-(chloromethyl)furfural-containing extraction solvent.

Without wishing to be bound by any kind of theory the heating in step (c) is believed to suitably result in the dehydration of at least part of the saccharides, present in the hydrochloric acid-containing, aqueous intermediate product solution, into 5-(chloromethyl)furfural.

Step (c) may or may not be carried out in the presence of a chloride containing promotor such as lithium chloride. Such lithium chloride may advantageously enhance the conversion of saccharides within the aqueous intermediate product solution.

In addition, the hydrochloric acid concentration may be adjusted. Additional hydrochloric acid may or may not be added; or additional water may or may not be added or removed. The later may help to obtain an optimum hydrochloric acid concentration for step (c).

Preferably step (c) comprises heating at least part of the hydrochloric acid-containing, aqueous intermediate product solution to a temperature equal to or more than 60° C., more preferably equal to or more than 70° C., yielding a product solution containing 5-(chloromethyl)furfural, whilst at the same time extracting the 5-(chloromethyl)furfural from such product solution into an extraction solvent. Part or whole of the produced 5-(chloromethyl)furfural can suitably be concurrently and/or simultaneously extracted from the product solution into an extraction solvent. Preferably at least part of the 5-(chloromethyl)furfural is removed continuously or semi-continuously via in-situ liquid-liquid extraction into such extraction solvent.

Preferably, step (c) is carried out in the presence of such an extraction solvent. More preferably, step (c) comprises heating at least part of the, hydrochloric acid-containing, aqueous intermediate product solution to a temperature equal to or more than 60° C., more preferably equal to or more than 70° C., in the presence of an extraction solvent, to thereby produce 5-(chloromethyl)furfural, and, preferably in-situ, extracting at least part of the produced 5-(chloromethyl)furfural into such extraction solvent, to thereby produce a 5-(chloromethyl)furfural-containing extraction solvent.

After conversion of the aqueous intermediate product solution, or more precisely the saccharides in the aqueous intermediate product solution, and the extraction of the 5-(chloromethyl)furfural from the, hydrochloric acid-containing, aqueous intermediate product solution, such solution can suitably become depleted from 5-(chloromethyl)furfural. Suitably merely a residual, hydrochloric acid-containing, aqueous solution remains. Such residual, hydrochloric acid-containing, aqueous solution may advantageously be recycled to step (a), optionally after removal of any impurities and/or optionally after reconcentration of the hydrochloric acid. That is, preferably a hydrochloric acid-containing, residual aqueous solution is obtained, and such, hydrochloric acid-containing, residual aqueous solution is recycled to step (a), optionally after adjusting the hydrochloric acid concentration.

Step (c) of the process according to the invention can suitably be carried out batch-wise, semi-continuously or continuously, in one or more reactor(s) and/or vessel(s). These one or more reactor(s) and/or vessel(s) are herein also referred to as dehydration reactor(s) and/or vessel(s). Preferably only one reactor is used in step (c). Step (c) can be carried out in an agitated dehydration reactor or in a non-agitated reactor with counter-flow as explained in more detail below.

The reactor can for example be a bubble reactor, a plug flow reactor, an external recycle loop reactor or a continuous stirred tank reactor (CSTR). The reactor can be agitated, for example by stirring or by using static mixing.

After the 5-(chloromethyl)furfural is produced, it can be separated from the reaction mixture resulting from step (c) by liquid-liquid extraction. Such liquid-liquid extraction can suitably be carried out in a separate extraction vessel subsequent to the dehydration reactor.

Preferably, however, such liquid-liquid extraction is carried out in-situ. By an in-situ extraction is herein understood that the 5-(chloromethyl)furfural is extracted into an extraction solvent present within the reaction mixture.

Preferably, the reactor in step (c) is therefore further suitable for carrying out a liquid-liquid extraction. For example, step (c) may comprise heating at least part of the, hydrochloric acid-containing, aqueous intermediate product solution, together with an extraction solvent, in an agitated (for example stirred or mixed) reactor, to a temperature equal to or more than 60° C., more preferably equal to or more than 70° C., to thereby produce 5-(chloromethyl)furfural. Subsequently at least part of such produced 5-(chloromethyl)furfural is extracted, in situ, into the extraction solvent, to thereby produce a 5-(chloromethyl)furfural-containing extraction solvent. Preferably such in-situ extraction is thus carried out continuously and/or simultaneously (i.e. alongside) with the dehydration reaction.

Advantageously step (c) is carried out in a continuously stirred tank reactor (CSTR). Suitably such CSTR may contain both (at least part of) the aqueous intermediate product solution as well as an extraction solvent. When applied in a continuous or semi-continuous process, such a CSTR may advantageously be combined with a separate continuous liquid-liquid separator, such as for example an in-line liquid-liquid separator using a hydrophobic membrane, a hydrocyclone or a swirl separator.

It can, however, also be advantageous to carry out step (c) in a, preferably biphasic, co-current or counter-current flow reactor, where a flow of at least part of the aqueous intermediate product solution is contacted, at a temperature of equal to or more than 60° C., more preferably equal to or more than 70° C., respectively co-currently or counter-currently, with a flow of extraction solvent.

Without wishing to be bound by any kind of theory, it is believed that by in-situ, and optionally counter-currently, contacting the aqueous intermediate product solution with the extraction solvent, the 5-(chloromethyl)furfural can be conveniently extracted into the extraction solvent, immediately after its preparation. That is, when the reaction is proceeding in the presence of the extraction solvent any 5-(chloromethyl)furfural can simultaneously be extracted into the extraction solvent.

Step (c) is advantageously carried out at a relatively high temperature, i.e. at a temperature equal to or more than 60° C., more preferably a temperature equal to or more than 70° C., and even more preferably a temperature equal to or more than 80° C. For practical purposes step (c) can suitably be carried out at a temperature in the range from equal to or more than 60° C., more preferably equal to or more than 70° C., even more preferably equal to or more than 80° C., to equal to or less than 120° C., more preferably equal to or less than 110° C.

Step (c) can be carried out at a wide range of pressures. Preferably, however, step (c) is carried out at a pressure in the range from 0.1 MegaPascal to 10.0 MegaPascal.

Preferably process step (c) is continued for a period ranging from equal to or more than 0.25 hours, more preferably from equal to or more than 0.50 hours, to equal to or less than 10.00 hours, more preferably to equal to or less than 4.00 hours, and still more preferably to equal to or less than 2.00 hours.

The extraction solvent is preferably an organic extraction solvent in which organic extraction solvent, at the temperature and pressure applied during step (c), 5-(chloromethyl)furfural has a higher solvability than in water.

The extraction solvent is preferably an organic extraction solvent:
which organic extraction solvent has a boiling temperature, at the pressure applied during step (c), which is lower than the temperature applied during step (c); and/or
which organic extraction solvent, at the temperature applied during step (c), is essentially immiscible with water; and/or
which organic extraction solvent, at the temperature and pressure applied during step (c), is essentially not reactive with hydrochloric acid.

By an organic extraction solvent is herein understood an extraction solvent comprising compounds having hydrocarbon bonds. By a hydrocarbon bond is herein understood a covalent bonding between a hydrogen and a carbon atom. By essentially immiscible with water is herein understood an organic extraction solvent having a solubility in water of less than 10 grams per 100 grams of water.

The extraction solvent can for example be a non-polar solvent or an aprotic polar solvent. Preferably the extraction solvent is an organic extraction solvent, more preferably an organic extraction solvent selected from the group consisting of: C6-C10 aromatic hydrocarbons, C1-C10 chlorinated hydrocarbons and C3-C10 ketones and mixtures of two or more thereof. By a Cx compound is herein understood a compound comprising "x" carbon atoms. By a Cx-Cz compound is herein understood a compound comprising in the range from "x" to "z" carbon atoms. Suitably the extraction solvent can be selected from the group consisting of: diethyl ether, diisopropyl ether, ethyl acetate, pentane, hexane, heptane, octane, decane, dodecane, cyclohexane, benzene, toluene, xylene, chloroform, dichloromethane, dichloroethane, carbon tetrachloride, trichloromethane (chloroform), methyl tert-butyl ether, and mixtures of two or more thereof. Most preferably an aromatic extraction solvent is used, more preferably selected from the group consisting of benzene, toluene and xylene.

When the heating in step (c) is carried out in the presence of the extraction solvent and when the 5-(chloromethyl)furfural is suitably extracted with such extraction solvent in-situ, an extraction solvent having a boiling point above 70° C. at the applied pressure is preferred.

More preferably the extraction solvent is therefore selected from the group consisting of heptane, octane, decane, dodecane, toluene, xylene, 1,2-dichloroethane, carbon tetrachloride and mixtures of two or more thereof.

Most preferably, the extraction solvent is toluene or 1,2-dichloroethane.

Preferably the volume ratio between the, hydrochloric acid-containing, aqueous intermediate product solution and the extraction solvent lies in the range from 10:1 to 1:10, more preferably in the range from 5:1 to 1:5.

Preferably the extraction solvent is either more or less dense than water. This allows the extraction solvent to be easily separated from water by simple phase separation. In addition this allows for a suitable operation in a, preferably biphasic, counter-current or co-current biphasic continuous flow reactor.

The yielded 5-(chloromethyl)furfural-containing extraction solvent can subsequently be separated from the aqueous intermediate product solution and/or the reaction mixture.

Such separation can be achieved in any manner known to be suitable therefore by the person skilled in the art. Such separation may or may not include cooling, phase separation, membrane separation, settling and/or centrifugation.

Any separated 5-(chloromethyl)furfural-containing extraction solvent may optionally be dried to remove any residual water.

To remove any residual 5-(chloromethyl)furfural from the remaining aqueous intermediate product solution and/or the reaction mixture, the remaining aqueous intermediate product solution and/or the reaction mixture may optionally be mixed and/or washed with additional extraction solvent to extract such residual 5-(chloromethyl)furfural.

Prefereably step (c) is carried out in a biphasic counter-current flow reactor, where a flow of at least part of the hydrochloric acid-containing, aqueous intermediate product solution is contacted counter-currently with a flow of extraction solvent. When a biphasic counter-current flow reactor is used, where a flow of at least part of the aqueous intermediate product solution is contacted counter-currently with a flow of extraction solvent, the 5-(chloromethyl)furfural-containing extraction solvent is already separated within the reactor from the aqueous intermediate product solution and/or the reaction mixture.

The 5-(chloromethyl)furfural may or may not be isolated from the 5-(chloromethyl)furfural-containing extraction solvent.

Preferably the process further comprises:
(i) isolating or separating the 5-(chloromethyl)furfural from the extraction solvent and converting the isolated or separated 5-(chloromethyl)furfural into 2,5 di-formylfuran, 5-(hydroxymethyl)furfural and/or an 5-(alkoxymethyl)furfural; or
(ii) retrieving the 5-(chloromethyl)furfural-containing extraction solvent, suitably as a whole, and converting the 5-(chloromethyl)furfural, in the presence of the extraction solvent, into 2,5 di-formylfuran, 5-(hydroxymethyl)furfural and/or an 5-(alkoxymethyl)furfural.

Preferably the 5-(chloromethyl)furfural is processed further in a non-isolated form, in combination with the extraction solvent. That is, preferably the 5-(chloromethyl)furfural-containing extraction solvent is further processed as a whole.

Alternatively, 5-(chloromethyl)furfural is first isolated from the extraction solvent, before further processing such 5-(chloromethyl)furfural.

The 5-(chloromethyl)furfural can be isolated from the extraction solvent in any manner known by the person skilled in the art, for example by evaporation and/or distillation. After removal of the 5-(chloromethyl)furfural, the extraction solvent may be recycled for re-use. The isolated 5-(chloromethyl)furfural may be converted with conventional techniques as known in the art into for example 2,5 di-formylfuran (DFF), 5-(hydroxymethyl)furfural (HMF) and/or 5-(alkoxymethyl)furfurals, such as 5-(methoxymethyl)furfural (MMF) or 5-(ethoxymethyl)furfural (EMF).

As indicated, advantageously it is not necessary to immediately isolate the 5-(chloromethyl)furfural from the extraction solvent. Any produced 5-(chloromethyl)furfural-containing extraction solvent may suitably be further processed without separating the 5-(chloromethyl)furfural.

For example, the extraction solvent can advantageously be used as a solvent in:
a process wherein the 5-(chloromethyl)furfural is reacted with an alkanol to produce an 5-(alkoxymethyl)furfural ether;
a process wherein the 5-(chloromethyl)furfural is reacted with water to produce 5-(hydroxymethyl)furfural; or
a process wherein the 5-(chloromethyl)furfural is converted into 2,5 di-formylfuran. When the 5-(chloromethyl)furfural is reacted with an alkanol, such alkanol is preferably selected from the group consisting of methanol, ethanol, propanol, iso-propanol, butanol, iso-butanol and tert-butanol.

The present invention therefore also provides a process for the production of 5-(alkoxymethyl)furfural comprising:
1) a process, which process includes the following steps:
 a) converting a solid material containing hemicellulose, cellulose and lignin, by:
  (i) hydrolyzing, at a temperature equal to or less than 30° C., at least part of the hemicellulose of the solid material with a first aqueous hydrochloric acid solution, which first aqueous hydrochloric acid solution has a hydrochloric acid concentration in the range from equal to or more than 15.0 wt. % to less than 40.0 wt. %, based on the weight amount of water and hydrochloric acid in such first aqueous hydrochloric acid solution, yielding a remaining solid material and a hydrochloric acid-containing, aqueous, first hydrolysate product solution;
  (ii) hydrolyzing, at a temperature equal to or less than 30° C., at least part of the cellulose of the remaining solid material with a second aqueous hydrochloric acid solution, which second aqueous hydrochloric acid solution has a hydrochloric acid concentration in the range from equal to or more than 40.0 wt. % to equal to or less than 51.0 wt. %, based on the weight amount of water and hydrochloric acid in such second aqueous hydrochloric acid solution, yielding a residue and a hydrochloric acid-containing, aqueous, second hydrolysate product solution.
(b) forwarding a, hydrochloric acid-containing, aqueous intermediate product solution comprising:
 a part of or the whole of the hydrochloric acid-containing, aqueous first hydrolysate product solution of step (a); and/or
 a part of or the whole of the, hydrochloric acid-containing, aqueous second hydrolysate product solution of step (a); and
(c) heating at least part of the hydrochloric acid-containing, aqueous intermediate product solution to a temperature equal to or more than 60° C., yielding a product solution containing 5-(chloromethyl)furfural, and extracting the 5-(chloromethyl)furfural from such product solution into an extraction solvent; and
further comprising:
2) retrieving the 5-(chloromethyl)furfural-containing extraction solvent; and
3) reacting the 5-(chloromethyl)furfural, in the presence of the extraction solvent, preferably at a temperature in the range from equal to or more than 10° C. to equal to or less than 90° C., more preferably equal to or less than 50° C., with an alkanol, preferably selected from the group consisting of ethanol, propanol, iso-propanol, butanol, iso-butanol and tert-butanol, suitably yielding an 5-(alkoxymethyl)furfural.

The step of retrieving the 5-(chloromethyl)furfural-containing extraction solvent can optionally be combined with step (c), for example when using a biphasic, co-current or counter-current, flow reactor. Further preferences for carrying out the reaction of the 5-(chloromethyl)furfural can be found for example in Estonian patent application EE2013/0003A. Most preferably the alkanol is ethanol, allowing the process to thereby produce 5-(ethoxymethyl)furfural (EMF). Further preferences for steps (a), (b) and (c) are as described herein above.

Further, the present invention also provides a process for the production of 5-(methoxymethyl)furfural comprising:
1) a process, which process includes the following steps:
 (a) converting a solid material containing hemicellulose, cellulose and lignin, by:
  (i) hydrolyzing, at a temperature equal to or less than 30° C., at least part of the hemicellulose of the solid material with a first aqueous hydrochloric acid solution, which first aqueous hydrochloric acid solution has a hydrochloric acid concentration in the range from equal to or more than 15.0 wt. % to less than 40.0 wt. %, based on the weight amount of water and hydrochloric acid in such first aqueous hydrochloric acid solution, yielding a remaining solid material and a hydrochloric acid-containing, aqueous, first hydrolysate product solution;
  (ii) hydrolyzing, at a temperature equal to or less than 30° C., at least part of the cellulose of the remaining solid material with a second aqueous hydrochloric acid solution, which second aqueous hydrochloric acid solution has a hydrochloric acid concentration in the range from equal to or more than 40.0 wt. % to equal to or less than 51.0 wt. %, based on the weight amount of water and hydrochloric acid in such second aqueous hydrochloric acid solution, yielding a residue and a hydrochloric acid-containing, aqueous, second hydrolysate product solution.

(b) forwarding to step (c) a, hydrochloric acid-containing, aqueous intermediate product solution comprising:
a part of or the whole of the hydrochloric acid-containing, aqueous first hydrolysate product solution of step (a); and/or
a part of or the whole of the, hydrochloric acid-containing, aqueous second hydrolysate product solution of step (a); and
(c) heating at least part of the hydrochloric acid-containing, aqueous intermediate product solution to a temperature equal to or more than 60° C., yielding a product solution containing 5-(chloromethyl)furfural, and extracting the 5-(chloromethyl)furfural from such product solution into an extraction solvent; and further comprising:
2) retrieving the 5-(chloromethyl)furfural-containing extraction solvent; and
3) reacting the 5-(chloromethyl)furfural, in the presence of the extraction solvent, preferably at a temperature in the range from equal to or more than 10° C. to equal to or less than 90° C., more preferably equal to or less than 50° C., with methanol, suitably yielding a 5-(methoxymethyl) furfural.

The step of retrieving the 5-(chloromethyl)furfural-containing extraction solvent can optionally be combined with step (c), for example when using a biphasic, co-current or counter-current, flow reactor. Further preferences for carrying out the reaction of the 5-(chloromethyl)furfural can be found for example in Estonian patent application EE2013/0003A. Further preferences for steps (a), (b) and (c) are as described herein above.

Still further, the present invention also provides a process for the production of 5-(hydroxymethyl)furfural comprising:
1) a process, which process includes the following steps:
a) converting a solid material containing hemicellulose, cellulose and lignin, by:
(i) hydrolyzing, at a temperature equal to or less than 30° C., at least part of the hemicellulose of the solid material with a first aqueous hydrochloric acid solution, which first aqueous hydrochloric acid solution has a hydrochloric acid concentration in the range from equal to or more than 15.0 wt. % to less than 40.0 wt. %, based on the weight amount of water and hydrochloric acid in such first aqueous hydrochloric acid solution, yielding a remaining solid material and a hydrochloric acid-containing, aqueous, first hydrolysate product solution;
(ii) hydrolyzing, at a temperature equal to or less than 30° C., at least part of the cellulose of the remaining solid material with a second aqueous hydrochloric acid solution, which second aqueous hydrochloric acid solution has a hydrochloric acid concentration in the range from equal to or more than 40.0 wt. % to equal to or less than 51.0 wt. %, based on the weight amount of water and hydrochloric acid in such second aqueous hydrochloric acid solution, yielding a residue and a hydrochloric acid-containing, aqueous, second hydrolysate product solution.
(b) forwarding to step (c) a, hydrochloric acid-containing, aqueous intermediate product solution comprising:
a part of or the whole of the hydrochloric acid-containing, aqueous first hydrolysate product solution of step (a); and/or
a part of or the whole of the, hydrochloric acid-containing, aqueous second hydrolysate product solution of step (a); and
(c) heating at least part of the hydrochloric acid-containing, aqueous intermediate product solution to a temperature equal to or more than 60° C., yielding a product solution containing 5-(chloromethyl)furfural, and extracting the 5-(chloromethyl)furfural from such product solution into an extraction solvent; and further comprising:
2) retrieving the 5-(chloromethyl)furfural-containing extraction solvent; and
3) reacting the 5-(chloromethyl)furfural, in the presence of the extraction solvent, preferably at a temperature in the range from equal to or more than 10° C. to equal to or less than 90° C., more preferably equal to or less than 50° C., with water, suitably yielding a 5-(hydroxymethyl)furfural.

The step of retrieving the 5-(chloromethyl)furfural-containing extraction solvent can optionally be combined with step (c), for example when using a biphasic, co-current or counter-current, flow reactor. Further preferences for steps (a), (b) and (c) are as described herein above.

Even further, the present invention also provides a process for the production of 2,5 di-formylfuran comprising:
1) a process, which process includes the following steps:
a) converting a solid material containing hemicellulose, cellulose and lignin, by:
(i) hydrolyzing, at a temperature equal to or less than 30° C., at least part of the hemicellulose of the solid material with a first aqueous hydrochloric acid solution, which first aqueous hydrochloric acid solution has a hydrochloric acid concentration in the range from equal to or more than 15.0 wt. % to less than 40.0 wt. %, based on the weight amount of water and hydrochloric acid in such first aqueous hydrochloric acid solution, yielding a remaining solid material and a hydrochloric acid-containing, aqueous, first hydrolysate product solution;
(ii) hydrolyzing, at a temperature equal to or less than 30° C., at least part of the cellulose of the remaining solid material with a second aqueous hydrochloric acid solution, which second aqueous hydrochloric acid solution has a hydrochloric acid concentration in the range from equal to or more than 40.0 wt. % to equal to or less than 51.0 wt. %, based on the weight amount of water and hydrochloric acid in such second aqueous hydrochloric acid solution, yielding a residue and a hydrochloric acid-containing, aqueous, second hydrolysate product solution.
(b) forwarding to step (c) a, hydrochloric acid-containing, aqueous intermediate product solution comprising:
a part of or the whole of the hydrochloric acid-containing, aqueous first hydrolysate product solution of step (a); and/or
a part of or the whole of the, hydrochloric acid-containing, aqueous second hydrolysate product solution of step (a); and
c) heating at least part of the hydrochloric acid-containing, aqueous intermediate product solution to a temperature equal to or more than 60° C., yielding a product solution containing 5-(chloromethyl)furfural, and extracting the 5-(chloromethyl)furfural from such product solution into an extraction solvent; and further comprising:
2) retrieving the 5-(chloromethyl)furfural-containing extraction solvent; and
3) oxydizing the 5-(chloromethyl)furfural, in the presence of the extraction solvent, to 2,5 di-formylfuran.

The step of retrieving the 5-(chloromethyl)furfural-containing extraction solvent can optionally be combined with step (c), for example when using a biphasic, co-current or counter-current, flow reactor. Further preferences for steps (a), (b) and (c) are as described herein above.

The above processes advantageously allows one to heat up and convert the saccharides resulting from hemicellulose and/or cellulose into useful products, without wasting energy on heating the lignin. In addition the above processes advantageously allow one to avoid any cumbersome and expensive steps to isolate the 5-(chloromethyl)furfural from the extraction solvent.

When producing a 5-(alkoxymethyl) furfural, a 5-(hydroxymethyl)furfural and/or diformylfurfural from the 5-(chloromethyl)furfural, hydrochloric acid is suitably again produced as a side-product. Such hydrochloric acid may advantageously be used in a direct recycle to step (a). More advantageously, such hydrochloric acid can be added as supplemental hydrochloric acid to a residual, hydrochloric acid-containing, aqueous solution being recycled from step (c) to step (a). Such recycles of hydrochloric acid and residual, hydrochloric acid-containing, aqueous solution reduce the making of chlorine-containing waste and contribute to the economics, efficiency and sustainability of the process of the invention.

Non-limiting FIGS. 1 and 2 below illustrates an example of the process according to the invention.

FIG. 1 shows a process according to the invention wherein step (a) is carried out as a two-staged process, comprising both a pre-hydrolysis stage as well as a main hydrolysis stage. Step (c) of the exemplified process is carried out continuously in the presence of an extraction solvent in a counter-current biphasic continuous flow reactor.

Step (a) of the illustrated process is carried out in a reactor sequence of 6 hydrolysis reactors (R1 to R6). The hydrolysis reactors are operated at a temperature of 20° C. and a pressure of 0.1 MegaPascal. The process is operated in a sequence of cycles, each cycle being carried out within a 8 hour cycle period.

FIG. 1 illustrates the start of a new cycle. At the start of a new cycle, dried wood chips (101) have just been loaded into reactor (R1) via solid inlet line (102). Reactor (R2) contains a (partly pre-hydrolyzed) solid material containing cellulose and lignin, wherein the hemicellulose fraction has already been partly hydrolyzed.

Reactor (R3) contains a remaining solid material containing predominantly cellulose and lignin that has already been fully pre-hydrolyzed. The solid material in reactors (R4) and (R5) is fully pre-hydrolyzed solid material, wherein the cellulose has already been partly hydrolyzed in the main-hydrolysis stage. In the solid material in reactor (R6) the cellulose fraction is fully hydrolyzed and represents a residue.

In FIG. 1 reactors (R1) and (R2) represent a pre-hydrolysis stage, whilst reactors (R3), (R4) and (R5) represent a further main hydrolysis stage and reactor (R6) represents a residue unloading stage.

The dried wood chips (101) in reactor (R1) are flooded with a plug (105c) of intermediate pre-hydrolysate solution coming from a storage vessel (103). This plug (105c) of intermediate pre-hydrolysate solution comprises an aqueous hydrochloric-acid solution that has taken up saccharides during a preceding cycle period in the process.

In a first part of the new cycle, a plug (105a) of fresh first aqueous hydrochloric acid solution, having a hydrochloric acid concentration of 37.0 wt % and containing essentially no saccharides yet, is introduced into reactor (R2), thereby pushing forward a plug (105b) of intermediate pre-hydrolysate solution, comprising an aqueous hydrochloric acid solution, but also containing already saccharides (i.e. derived from the hemicellulose fraction of the solid material that was residing in reactor (R2)), from reactor (R2) into reactor (R1). The plug (105b) of intermediate pre-hydrolysate solution pushes the plug (105d) out from reactor (R1). Plug (105d) previously contained intermediate pre-hydrolysate solution, but has now taken up sufficient saccharides and has become a final first hydrolysate product solution. Such final first hydrolysate product solution can suitably be forwarded to one or more subsequent processes or devices.

During the same first part of the cycle, a plug (106a) of fresh second aqueous hydrochloric acid solution, having a hydrochloric acid concentration of 42.0 wt % and containing essentially no saccharides yet, is introduced into reactor (R5), thereby pushing forward a plug (106b) of intermediate hydrolysate solution, comprising an aqueous hydrochloric acid solution, but also containing already saccharides (i.e. derived from the cellulose fraction of the solid material that was residing in reactor (R5)), from reactor (R5) into reactor (R4). This plug (106b) in its turn pushes forward a second plug (106c) of intermediate hydrolysate solution, comprising an aqueous hydrochloric acid solution, but also containing saccharides (i.e. derived from the cellulose fraction of the solid material that was residing in previous reactors (R4) and (R5)), from reactor (R4) into reactor (R3). Plug (106c) pushes a plug (106d) of final, -hydrochloric acid-containing, aqueous second hydrolysate product solution out of reactor (R3). Whilst being pushed from reactor (R5) into reactor (R4) and further into reactor (R3), the intermediate hydrolysate solution absorbs more and more saccharides from the solid material remaining in such reactors from previous stages. The saccharide concentration of the intermediate hydrolysate solution advantageously increases, thus allowing a saccharide concentration to be obtained, that is higher than the saccharide concentration obtained in a batch-process.

The plug (106d) of final, hydrochloric acid-containing, aqueous second hydrolysate product solution pushed out of reactor (R3) is conveniently forwarded via liquid outlet line (112) to a counter-current biphasic continuous flow reactor (114).

During this same part of the cycle, residue (107) containing lignin can suitably be removed from reactor (R6) via solid outlet line (108).

In a second part of the cycle (not illustrated), intermediate hydrolysate solution is withdrawn from reactor (R5) and pushed into reactor (R4), separating intermediate hydrolysate solution from a residue, which residue is left behind in reactor (R5). The plug of withdrawn intermediate hydrolysate solution withdrawn from reactor (R5) and pushed into reactor (R4) pushes forward the plugs in the reactors (R4) and (R3). The plug of intermediate hydrolysate solution residing in reactor (R3) is pushed out of reactor (R3) into reactor (R2). The plug of intermediate pre-hydrolysate solution residing in reactor (R2) is pushed out of reactor (R2) into reactor (R1). The plug (105e) of intermediate pre-hydrolysate solution residing in reactor (R1) is pushed out of reactor (R1) into storage vessel (103). At the same time reactor (R6) can be loaded with a new batch dried wood chips. The cycle has now been completed and all reactors have shifted one position in the reactor sequence. That is, reactor (R6) has shifted into the position of reactor (R1). Reactor (R1) has shifted into the position of reactor (R2). Reactor (R2) has shifted into the position of reactor (R3).

Reactor (R3) has shifted into the position of reactor (R4). Reactor (R4) has shifted into the position of reactor (R5) and reactor (R5) has shifted into the position of reactor (R6).

Figure 2:
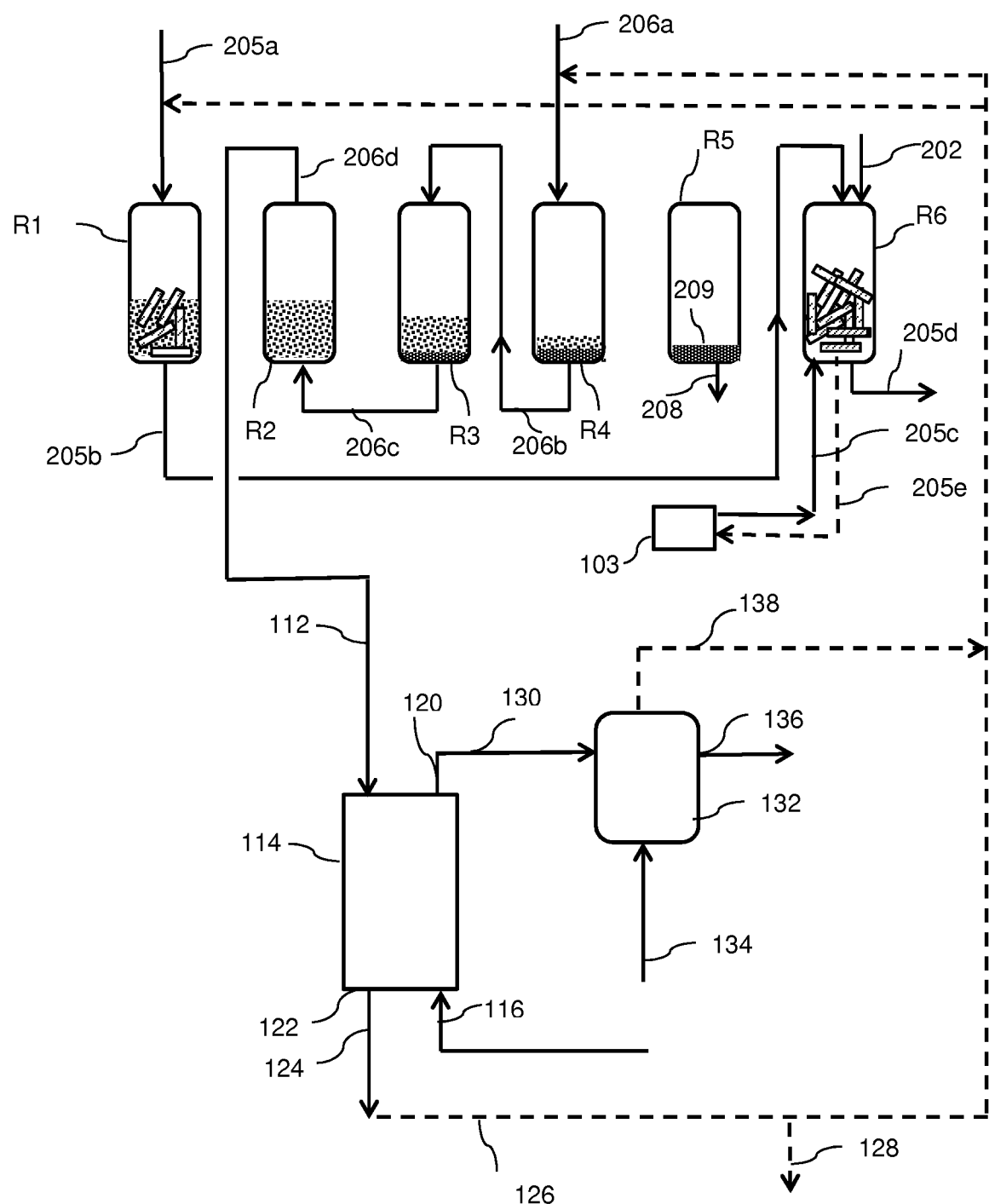
FIG. 2 illustrates a second cycle, starting at a time "t+8 hours" of the same process as FIG. 1.

The situation wherein all reactors have shifted one position has been illustrated in FIG. 2. FIG. 2 illustrates the start of a subsequent cycle, at a time "t+8 hours". The dried wood chips in reactor (R6) can be flooded with a plug (204c) of intermediate pre- hydrolysate solution withdrawn from the storage vessel (103). This is the same intermediate pre-hydrolysate solution that was stored in such storage vessel (103) in the second part of the previous cycle. The subsequent cycle can be carried out in a similar manner as described above for the preceding cycle, where numerals (201), (202), (205a-e) and (206a-d) refer to features similar to the features referred to by numerals (101), (102), (105a-e) and (106a-d) in FIG. 1. After a total of 6 cycles, and a period of 48 hours, the situation is again exactly as in FIG. 1.

It is noted that all pre-hydrolysate and hydrolysate solutions in the above examples are suitably aqueous hydrolysate solutions, respectively aqueous pre-hydrolysate solutions.

In the above, all the hydrochloric acid concentrations are on a weight basis, based on the combined weight amount of water and hydrochloric acid.

As described above, final, hydrochloric acid-containing, aqueous second hydrolysate solution (106d), respectively (206d) is pushed out of reactor (R3) and forwarded via liquid outlet line (112) to a counter-current biphasic continuous flow reactor (114). In such counter-current biphasic continuous flow reactor, the hydrochloric acid-containing, aqueous hydrolysate solution is subsequently contacted with an extraction solvent, such as toluene, supplied via liquid inlet line (116). The counter-current biphasic continuous flow reactor (114) is operated at 90° C.

From the top of the counter-current biphasic continuous flow reactor (114) a stream of 5-(chloromethyl)furfural-containing extraction solvent (120) is obtained via liquid outlet line (130) and from the bottom of the counter-current biphasic continuous flow reactor (114) a stream comprising residual, hydrochloric acid-containing, aqueous solution (122) is obtained via liquid outlet line (124).

The bottom stream (122) comprising residual, hydrochloric acid-containing aqueous solution is optionally recycled via recycle line (126) (illustrated as a dashed line) to be reused as at least part of the first or second hydrochloric acid solution described above. If so desired, minor impurities can be removed and optionally a bleed stream (128) can be present (illustrated as a dashed line).

The top stream of reactor (114) of 5-(chloromethyl) furfural-containing extraction solvent (120) is forwarded via liquid outlet line (130) to a further reactor (132). In the further reactor (132) the 5-(chloromethyl)furfural is reacted with ethanol provided via liquid inlet line (134) at a temperature of 50° C. to thereby produce 5-(ethoxymethyl) furfural and a hydrochloric acid side-product. The 5-(ethoxymethyl)furfural can be withdrawn from reactor (132) via liquid outlet line (136) and processed further. The hydrogen chloride containing side-product can conveniently be recycled via recycle line (138) to be reused as supplemental hydrochloric acid to produce at least part of the first or second hydrochloric acid solution described above.

The invention is further illustrated by the following non-limiting examples.

EXAMPLE 1

Hydrolysis of Pine Wood

In a first hydrolysis step, hereafter called prehydrolysis step, about 1150 grams of dried pine wood chips, having a particle size as determined by visual inspection of about 4-5 centimeters, was divided over 5 tubular reactors, each tubular reactor having a height of about 60 centimeters and a diameter of about 5.3 centimeters. The pine wood contained about 30.6 wt % cellulose, about 13.7% hemicellulose and about 30.6 wt % lignin, with the remainder being other compounds.

The pine wood chips were treated with a liquid column of about 8.7 liter of an aqueous solution containing about 37 wt % hydrochloric acid (HCl) in a semi-continuous manner such that in each reactor the pine wood chips were treated for about 16 hours. After treatment the liquid was separated from the remaining solid material by means of a glass filter plate pore size class 0 (i.e. having a nominal pore size of 160-250 μm), resulting in about 5.9 liter of a hydrochloric acid-containing, aqueous, first hydrolysate product solution, hereafter called pre-hydrolysate product.

The remaining solid material was treated with a liquid column of about 5.1 liter of an aqueous solution containing about 42 wt % hydrochloric acid (HCl) in a semi-continuous manner such that in each reactor the remaining solid material was treated for about 24 hours. After treatment the liquid was separated from the remaining residue by means of a glass filter plate pore size class 0 (i.e. having a nominal pore size of 160-250 μm), resulting in about 4.9 liter of a hydrochloric acid-containing, aqueous, second hydrolysate product solution, hereafter called main hydrolysate product.

The composition of the prehydrolysate product and main hydrolysate product was determined by ion exchange chromatography. Of each of the prehydrolysate procduct and the main hydrolysate product two samples were taken and the content (in weight percentage (wt %) of the different sugar components was determined. Table 1 below lists the average of the two determinations. The main hydrolysate product and the prehydrolysate product were both essentially lignin-free.

TABLE 1

Composition prehydrolysate product and main hydrolysate product

|  | Main hydrolysate product (sugars in wt %) | Prehydrolysate product (sugars in wt %) |
| --- | --- | --- |
| Sorbitol | 0.000 | 0.000 |
| Mannitol | 0.034 | 0.032 |
| Fructose | 0.000 | 0.000 |
| Arabinose | 0.196 | 0.410 |
| Rhamnose | 0.000 | 0.000 |
| Galactose | 0.261 | 0.455 |
| Glucose | 5.628 | 0.616 |
| Xylose | 0.446 | 0.913 |
| Mannose | 1.412 | 1.467 |
| Fructose | 0.000 | 0.000 |

EXAMPLE 2

Conversion of Prehydrolysate Product

A sample of 0.5 ml of the prehydrolysate product obtained in example 1 was combined with 1 ml toluene and loaded in an 8 ml reactor using magnetic stirring at 1600 rounds per minute (rpm). The reaction mixture was heated to 100° C. for 1 hour. Subsequently the reaction was quenched by placing the reactor in ice and separated into a toluene layer and an aqueous layer. The aqueous layer was washed 2 times with 0.5 ml of fresh toluene. Subsequently the toluene layers were combined and analyzed by Gas Chromatography (GC)

using dioxane as internal standard, to determine the yields of furfural and 5-(chloromethyl)furfural (CMF). The aqueous layer was analyzed for remaining sugars by ion exchange chromatography and High Performance Liquid Chromatography, (HPLC). The aqueous phase further contained levulinic acid as determined h HPLC.

The yields of furfural and CMF in weight percentages (wt %), based on the total weight of sugars in the 0.5 ml sample, were determined and are summarized in Table 2 below.

EXAMPLE 3

Conversion of Main Hydrolysate Product

A sample of 0.5 ml of the main hydrolysate product obtained in example 1 was combined with 1 ml toluene and loaded in an 8 ml reactor using magnetic stirring at 1600 rounds per minute (rpm). In a manner identical to example 2, the reaction mixture was heated to 100° C. for 1 hour. Subsequently the reaction was quenched by placing the reactor in ice and separated into a toluene layer and an aqueous layer. The aqueous layer was washed 2 times with 0.5 ml of fresh toluene. Subsequently the toluene layers were combined and analyzed by Gas Chromatography (GC) using dioxane as internal standard, to determine the yields of furfural and 5-(chloromethyl)furfural (CMF). The aqueous layer was analyzed for remaining sugars by ion exchange chromatography and HPLC.

The yields of furfural and CMF in weight percentages (wt %), based on the total weight of sugars in the 0.5 ml sample, were determined and are summarized in Table 2 below.

TABLE 2

Furfural and CMF yield, based on total sugar content in the samples

| Example | Feed | Furfural yield (wt %, based on total sugar content in the sample) | CMF yield (wt %, based on total sugar content in the sample) |
|---|---|---|---|
| 2 | 0.5 ml prehydrolysate product and 1 ml toluene | 3.5 | 10.5 |
| 3 | 0.5 ml main hydrolysate product and 1 ml toluene | 0.3 | 27.0 |

As shown by Table 2, the process according to the invention allows one to be flexible in the co-production of furfural and CMF, depending on market demand for each of these products. The flexibility to amend the co-production of furfural and CMF can be achieved by including a part of or the whole of the prehydrolysate product and/or a part or the whole of the main hydrolysate product in the process at elevated temperature (in this example illustrated at 100° C.) and extracting the products into an extraction solvent (in this example illustrated by toluene).

The above also illustrates that advantageously one can only use the main hydrolysate product in step (c), allowing one to use at least part of the prehydrolysate product to produce other valuable products, such as xylitol from xylose. In this manner a more efficient use of the wood saccharides can be made.

EXAMPLES 4-9

Conversion of 5-Chloromethylfurfural

An amount of 5-Chloromethylfurfural (CMF) as listed in Table 3 was weighed in 1.8 mL HPLC vials and dissolved in an amount of dichloromethane (DCM) solvent as listed in Table 3. To such solution of CMF in dichloromethane solvent, methanol (MeOH) was added in an amount as listed in Table 3. Directly after addition of the methanol to the reaction mixture, the vials were heated to a temperature (T) as listed in Table 3 to start the reaction. After a reaction time (t) as listed in Table 3, the vials were directly cooled in an ice bath, followed by work-up for analysis (gas chromatography and ultra performance liquid chromatography).

Table 3 provides an overview of the conversion of 5-Chloromethylfurfural (CMF) and the yields and selectivity towards 5-(methoxymethyl)furfural (MMF).

TABLE 3

| Example | Amount CMF (mg) | T (° C.) | t (h) | DCM (μL) | MeOH (μL) | Yield MMF (mol %) | Conversion CMF (mol %) | Selectivity MMF (mol %) |
|---|---|---|---|---|---|---|---|---|
| 4 | 10.1 | 50 | 4 | 350 | 150 | 84.6 | 97.5 | 86.8 |
| 5 | 10.9 | 50 | 4 | 250 | 250 | 79.7 | 98.6 | 80.8 |
| 6 | 11.5 | 50 | 2 | 250 | 250 | 78.5 | 98.2 | 79.9 |
| 7 | 10.3 | 30 | 4 | 250 | 250 | 73.3 | 98.5 | 74.4 |
| 8 | 11.7 | 50 | 2 | 350 | 150 | 64.7 | 91.9 | 70.3 |
| 9 | 11.9 | 30 | 3 | 250 | 250 | 57.4 | 60.6 | 94.7 |

The invention claimed is:

1. A process, which process includes the following steps:
   (a) converting a solid material containing hemicellulose, cellulose and lignin, by:
   (i) hydrolyzing, at a temperature equal to or less than 40° C., at least part of the hemicellulose of the solid material with a first aqueous hydrochloric acid solution, which first aqueous hydrochloric acid solution has a hydrochloric acid concentration in the range from equal to or more than 15.0 wt. % to less than 40.0 wt. %, based on the weight amount of water and hydrochloric acid in such first aqueous hydrochloric acid solution, yielding a remaining solid material and a hydrochloric acid-containing, aqueous, first hydrolysate product solution comprising at least one compound selected from the group consisting of mannose, glucose, galactose, arabinose and xylose or their dimers or oligomers;
   (ii) hydrolyzing, at a temperature equal to or less than 40° C., at least part of the cellulose of the remaining solid material with a second aqueous hydrochloric acid solution, which second aqueous hydrochloric acid solution has a hydrochloric acid concentration in the range from equal to or more than 40.0 wt. % to equal to or less than 51.0 wt. %, based on the weight amount of water and hydrochloric acid in such second aqueous hydrochloric acid solution, yielding a residue and a hydrochloric acid-containing, aqueous, second hydrolysate product solution comprising glucose saccharides;

(b) forwarding to step (c) a, hydrochloric acid-containing, aqueous intermediate product solution comprising:
a part of or the whole of the hydrochloric acid-containing, aqueous first hydrolysate product solution of step (a); and/or
a part of or the whole of the, hydrochloric acid-containing, aqueous second hydrolysate product solution of step (a); and
(c) heating at least part of the hydrochloric acid-containing, aqueous intermediate product solution to a temperature equal to or more than 60° C., yielding a product solution containing 5-(chloromethyl)furfural, and extracting the 5-(chloromethyl)furfural from such product solution into an organic extraction solvent which extraction solvent extracts part or all of the 5-(chloromethyl)furfural from the product solution into the extraction solvent and is immiscible with water at the temperature applied during step (c).

2. The process according to claim 1, wherein step (a) is carried out in a plurality of reactors, connected in series, comprising in the range from equal to or more than 2 to equal to or less than 16 reactors.

3. The process according to claim 1, wherein step (a) is carried out in a plurality of reactors:
wherein one or more portions of first aqueous hydrochloric acid solution are moving from one reactor to another and are contacted with stationary solid material residing in such reactors; and/or
wherein one or more portions of second aqueous hydrochloric acid solution are moving from one reactor to another and are contacted with stationary remaining solid material residing in such reactors.

4. The process according to claim 1,
wherein the first aqueous hydrochloric acid solution is contacted counter-currently with the solid material and/or
wherein the second aqueous hydrochloric acid solution is contacted counter-currently with the remaining solid material.

5. The process according to claim 1, wherein in step (i) one or more portions of first aqueous hydrochloric acid solution form a plug or liquid column, optionally in combination with other fluids, which plug or liquid column is moving through a plurality of reactors, each reactor containing an amount of stationary solid material.

6. The process according to claim 1, wherein in step (ii) one or more portions of second aqueous hydrochloric acid solution form a plug or liquid column, optionally in combination with other fluids, which plug or liquid column is moving through a plurality of reactors, each reactor containing an amount of stationary remaining solid material.

7. The process according to claim 1, wherein in step (c) part or whole of the 5-(chloromethyl)furfural is concurrently extracted from the product solution into the extraction solvent.

8. The process according to claim 1, wherein step (c) is carried out in a biphasic counter-current flow reactor, where a flow of at least part of the hydrochloric acid-containing, aqueous intermediate product solution is contacted counter-currently with a flow of extraction solvent.

9. The process according to claim 1, wherein the extraction solvent comprises toluene and/or 1,2-dichloroethane.

10. The process according to claim 1, wherein step (c) is carried out at a temperature equal to or more than 70° C.

11. The process according to claim 1, wherein the process further comprises separating the 5-(chloromethyl)furfural from the extraction solvent and optionally recycling the extraction solvent.

12. The process according to claim 1, wherein the process further comprises:
(i) isolating the 5-(chloromethyl)furfural from the extraction solvent and converting the isolated 5-(chloromethyl)furfural into 2,5 di-formylfuran, 5-(hydroxymethyl)furfural and/or 5-(alkoxymethyl)furfural; or
(ii) retrieving the 5-(chloromethyl)furfural-containing extraction solvent and converting the 5-(chloromethyl)furfural, in the presence of the extraction solvent, into 2,5 di-formylfuran, 5-(hydroxymethyl)furfural and/or an 5-(alkoxymethyl)furfural.

13. The process according to claim 1, comprising:
retrieving the 5-(chloromethyl)furfural-containing extraction solvent; and
reacting the 5-(chloromethyl)furfural, in the presence of the extraction solvent with ethanol yielding an 5-(alkoxymethyl)furfural.

14. The process according to claim 1, further comprising:
retrieving the 5-(chloromethyl)furfural-containing extraction solvent; and
reacting the 5-(chloromethyl)furfural, in the presence of the extraction solvent with methanol, yielding a 5-(methoxymethyl)furfural.

15. The process according to claim 1, further comprising:
retrieving the 5-(chloromethyl)furfural-containing extraction solvent; and
reacting the 5-(chloromethyl)furfural, in the presence of the extraction solvent, with water, yielding a 5-(hydroxymethyl)furfural.

16. The process according to claim 1, further comprising:
retrieving the 5-(chloromethyl)furfural-containing extraction solvent; and
oxidizing the 5-(chloromethyl)furfural, in the presence of the extraction solvent, to 2,5 di-formylfuran.

17. The process according to claim 1, wherein in step (i) at least part of the hemicellulose of the solid material is hydrolyzed at a temperature equal to or less than 30° C.

18. The process according to claim 1, wherein in step (ii) at least part of the cellulose of the remaining solid material is hydrolyzed at a temperature equal to or less than 30° C.

19. The process according to claim 5, wherein in step (i) the plug or liquid column is moving continuously or semi-continuously through a plurality of reactors.

20. The process according to claim 6, wherein in step (ii) the plug or liquid column is moving continuously or semi-continuously through a plurality of reactors.

21. The process according to claim 13, wherein the 5-(chloromethyl)furfural is reacted with ethanol yielding an 5-(alkoxymethyl)furfural at a temperature in the range from equal to or more than 10° C. to equal to or less than 90° C.

22. The process according to claim 21, wherein the 5-(chloromethyl)furfural is reacted with ethanol yielding an 5-(alkoxymethyl)furfural at a temperature in the range from equal to or more than 10° C. to equal to or less than 50° C.

23. The process according to claim 14, wherein the 5-(chloromethyl)furfural is reacted with methanol yielding a 5-(methoxymethyl)furfural at a temperature in the range from equal to or more than 10° C. to equal to or less than 90° C.

24. The process according to claim 23, wherein the 5-(chloromethyl)furfural is reacted with methanol yielding a 5-(methoxymethyl)furfural at a temperature in the range from equal to or more than 10° C. to equal to or less than 50° C.

25. The process according to claim 15, wherein the 5-(chloromethyl)furfural is reacted with water yielding a 5-(hydroxymethyl)furfural.at a temperature in the range from equal to or more than 10° C. to equal to or less than 90° C.

26. The process according to claim 25, wherein the 5-(chloromethyl)furfural is reacted with water yielding a 5-(hydroxymethyl)furfural at a temperature in the range from equal to or more than 10° C. to equal to or less than 50° C.

\* \* \* \* \*